(12) United States Patent
Voit et al.

(10) Patent No.: US 9,546,112 B2
(45) Date of Patent: Jan. 17, 2017

(54) METHODS OF INCREASING EFFICIENCY OF VECTOR PENETRATION OF TARGET TISSUE

(75) Inventors: Thomas Voit, London (GB); Luis Garcia, Noisy-le-Roi (FR); Jérôme Denard, Choisy Le Roi (FR); Fedor Svinartchouk, Villejuif (FR)

(73) Assignees: ASSOCIATION INSTITUT DE MYOLOGIE (FR); GÉNÉTHON (FR); CENTRE NATIONAL DE LA RECHERCHE SCIENTIFIQUE (FR); UNIVERSITÉ PIERRE ET MARIE CURIE (PARIS 6) (FR); INSTITUT NATIONAL DE LA SANTÉ ET DE LA RECHERCHE MÉDICALE (FR)

( * ) Notice: Subject to any disclaimer, the term of this patent is extended or adjusted under 35 U.S.C. 154(b) by 1 day.

(21) Appl. No.: 13/636,596

(22) PCT Filed: Mar. 22, 2011

(86) PCT No.: PCT/EP2011/054378
§ 371 (c)(1),
(2), (4) Date: Apr. 10, 2013

(87) PCT Pub. No.: WO2011/117258
PCT Pub. Date: Sep. 29, 2011

(65) Prior Publication Data
US 2013/0189225 A1    Jul. 25, 2013

Related U.S. Application Data

(60) Provisional application No. 61/316,302, filed on Mar. 22, 2010.

(51) Int. Cl.
*C12N 15/00* (2006.01)
*A61K 35/12* (2015.01)
(Continued)

(52) U.S. Cl.
CPC ............ *C04B 35/10* (2013.01); *A61K 31/522* (2013.01); *A61K 38/00* (2013.01);
(Continued)

(58) Field of Classification Search
None
See application file for complete search history.

(56) References Cited

U.S. PATENT DOCUMENTS

| 6,046,314 A * | 4/2000 | Gebe et al. .................. 536/23.1 |
| 2005/0123539 A1 * | 6/2005 | Rusnak ..................... 424/144.1 |

(Continued)

FOREIGN PATENT DOCUMENTS

| WO | 00/75365 A2 | 12/2000 |
| WO | 02/063025 A2 | 8/2002 |

OTHER PUBLICATIONS

Grassadonia et al., "90K (Mac-2 BP) and galectins in tumor progression and metastasis," Glycoconjugate Journal 19, 551-556 (2004).*

Goncalves et al., "Molecular cloning and analysis of SSc5D, a new member of the scavenger receptor cysteine-rich superfamily," Mol Immunol 46(13): 2585-96 (2009).*

(Continued)

*Primary Examiner* — Janet L Andres
*Assistant Examiner* — M. Franco Salvoza
(74) *Attorney, Agent, or Firm* — Leason Ellis LLP

(57) ABSTRACT

Methods for increasing the efficiency of target tissue penetration of an adeno-associated virus (AAV) vector in a patient are provided. In some aspects, the methods involve inhibiting the interaction of the serum protein galectin 3 binding protein (G3BP) with AAV vector. Further provided are methods for reducing tissue distribution of a virus or for neutralizing a virus harbored by an organ destined for transplant, or newly transplanted, by administering a composition comprising G3BP.

2 Claims, 15 Drawing Sheets

(51) Int. Cl.

| | | |
|---|---|---|
| A61N 1/30 | (2006.01) | |
| C04B 35/10 | (2006.01) | |
| A61K 38/17 | (2006.01) | |
| A61K 38/21 | (2006.01) | |
| A61K 45/06 | (2006.01) | |
| C07K 16/08 | (2006.01) | |
| C07K 16/18 | (2006.01) | |
| C12N 15/86 | (2006.01) | |
| A61K 31/522 | (2006.01) | |
| A61K 38/00 | (2006.01) | |
| A61K 48/00 | (2006.01) | |
| C04B 35/14 | (2006.01) | |
| C04B 35/565 | (2006.01) | |
| C04B 35/622 | (2006.01) | |
| C07K 14/005 | (2006.01) | |
| C12N 7/00 | (2006.01) | |

(52) U.S. Cl.
CPC .......... *A61K 38/1709* (2013.01); *A61K 38/21* (2013.01); *A61K 45/06* (2013.01); *A61K 48/0058* (2013.01); *C04B 35/14* (2013.01); *C04B 35/565* (2013.01); *C04B 35/622* (2013.01); *C07K 14/005* (2013.01); *C07K 16/081* (2013.01); *C07K 16/18* (2013.01); *C12N 7/00* (2013.01); *C12N 15/86* (2013.01); *A61K 48/0008* (2013.01); *C12N 2750/14122* (2013.01); *C12N 2750/14143* (2013.01); *C12N 2750/14145* (2013.01); *C12N 2750/14151* (2013.01); *C12N 2810/6027* (2013.01)

(56) References Cited

U.S. PATENT DOCUMENTS

| | | | |
|---|---|---|---|
| 2010/0055723 A1* | 3/2010 | Smalley et al. | 435/7.92 |
| 2012/0003157 A1* | 1/2012 | Iacobelli | 424/9.1 |
| 2012/0121590 A1* | 5/2012 | Ley et al. | 424/134.1 |

OTHER PUBLICATIONS

Hartshorn et al., "Salivary agglutinin and lung scavenger receptor cysteine rich-glycoprotein 340 have broad anti-influenza activities and interactions with surfactant protein D that vary according to donor source and sialyation," Biochem J 15: 393 (Pt 2): 545-53 (2006).*

Cannon et al., "HIV envelope binding by macrophage-expressed gp340 promotes HIV-1 infection," J Immunol 181(30): 2065-70 (2008).*

Breitbart et al., "Viral diversity and dynamics in an infant gut," Research in Microbiology 159: 367-373 (2008).*

Artini et al., "Elevated serum levels of 90K/MAC-2BP predict unresponsiveness to α-interferon therapy in chronic HCV hepatitis patients," Journal of Hepatology 25: 212-217 (1996).*

Rudikoff et al., "Single amino acid substitution altering antigen-binding specificity," PNAS vol. 79: 1979-1983 (1982).*

Schultz et al., "Recombinant Adeno-associated Virus Transduction and Integration," Molecular Therapy, vol. 16, No. 7: 1189-1199 (2008).*

Liu et al., "Comparative biology of rAAV transduction in ferret, pig and human airway epithelia," Gene Therapy 14: 1543-1548 (2007).*

Ullrich et al., "The Secreted Tumor-Associated Antigen 90k Is a Potent Immune Stimulator," The Journal of Biological Chemistry, vol. 269, No. 28: 18401-18407 (1994).*

International Search Report for International Application No. PCT/EP2011/04378 mailed Nov. 10, 2011.

Smalley et al. "Proteomic discovery of 21 proteins expressed in human plasma-derived but not platelet-derived microparticles." Thrombosis and Haemostatis, Schattauer GmbH. vol. 97, No. 1. Jan. 1, 2007. pp. 67-80.

Wu et al. "Single amino acid changes can influence titer, heparin binding, and tissue tropism in different adeno-associated virus serotypes." Journal of Virology, vol. 80, No. 22, Nov. 2006. pp. 11393-11397.

Zaiss et al. "Complement is an essential component of the immune response to adeno-associated virus vectors." Journal of Virology, vol. 82, No. 6. Mar. 2008. pp. 2727-2740.

* cited by examiner

AAV1 : SEQ ID NO 6
AAV6 : SEQ ID NO 4

```
              1                                                           60
AAV1   (1)   MAADGYLPDWLEDNLSEGIREWWDLKPGAPKPKANQQKQDDGRGLVLPGYKYLGPFNGLD
AAV6   (1)   MAADGYLPDWLEDNLSEGIREWWDLKPGAPKPKANQQKQDDGRGLVLPGYKYLGPFNGLD
              61                                                          120
AAV1   (61)  KGEPVNAADAAALEHDKAYDQQLKAGDNPYLRYNHADAEFQERLQEDTSFGGNLGRAVFQ
AAV6   (61)  KGEPVNAADAAALEHDKAYDQQLKAGDNPYLRYNHADAEFQERLQEDTSFGGNLGRAVFQ
              121                                                         180
AAV1   (121) AKKRVLEPLGLVEEGAKTAPGKKRPVEQSPQEPDSSSGIGKTGQQPAKKRLNFGQTGDSE
AAV6   (121) AKKRVLEPFGLVEEGAKTAPGKKRPVEQSPQEPDSSSGIGKTGQQPAKKRLNFGQTGDSE
              181                                                         240
AAV1   (181) SVPDPQPLGEPPATPAAVGPTTMASGGGAPMADNNEGADGVGNASGNWHCDSTWLGDRVI
AAV6   (181) SVPDPQPLGEPPATPAAVGPTTMASGGGAPMADNNEGADGVGNASGNWHCDSTWLGDRVI
              241                                                         300
AAV1   (241) TTSTRTWALPTYNNHLYKQISSASTGASNDNHYFGYSTPWGYFDFNRFHCHFSPRDWQRL
AAV6   (241) TTSTRTWALPTYNNHLYKQISSASTGASNDNHYFGYSTPWGYFDFNRFHCHFSPRDWQRL
              301                                                         360
AAV1   (301) INNNWGFRPKRLNFKLFNIQVKEVTTNDGVTTIANNLTSTVQVFSDSEYQLPYVLGSAHQ
AAV6   (301) INNNWGFRPKRLNFKLFNIQVKEVTTNDGVTTIANNLTSTVQVFSDSEYQLPYVLGSAHQ
              361                                                         420
AAV1   (361) GCLPPFPADVFMIPQYGYLTLNNGSQAVGRSSFYCLEYFPSQMLRTGNNFTFSYTFEEVP
AAV6   (361) GCLPPFPADVFMIPQYGYLTLNNGSQAVGRSSFYCLEYFPSQMLRTGNNFTFSYTFEDVP
              421                                                         480
AAV1   (421) FHSSYAHSQSLDRLMNPLIDQYLYYLNRTQNQSGSAQNKDLLFSRGSPAGMSVQPKNWLP
AAV6   (421) FHSSYAHSQSLDRLMNPLIDQYLYYLNRTQNQSGSAQNKDLLFSRGSPAGMSVQPKNWLP
              481                                                         540
AAV1   (481) GPCYRQQRVSKTKTDNNNSNFTWTGASKYNLNGRESIINPGTAMASHKDDEDKFFPMSGV
AAV6   (481) GPCYRQQRVSKTKTDNNNSNFTWTGASKYNLNGRESIINPGTAMASHKDLKDKFFPMSGV
              541                                                         600
AAV1   (541) MIFGKESAGASNTALDNVMITDEEEIKATNPVATERFGTVAVNFQSSSTDPATGDVHAMG
AAV6   (541) MIFGKESAGASNTALDNVMITDEEEIKATNPVATERFGTVAVNLQSSSTDPATGDVHVMG
              601                                                         660
AAV1   (601) ALPGMVWQDRDVYLQGPIWAKIPHTDGHFHPSPLMGGFGLKNPPPQILIKNTPVPANPPA
AAV6   (601) ALPGMVWQDRDVYLQGPIWAKIPHTDGHFHPSPLMGGFGLKHPPPQILIKNTPVPANPPA
              661                                                         720
AAV1   (661) EFSATKFASFITQYSTGQVSVEIEWELQKENSKRWNPEVQYTSNYAKSANVDFTVDNNGL
AAV6   (661) EFSATKFASFITQYSTGQVSVEIEWELQKENSKRWNPEVQYTSNYAKSANVDFTVDNNGL
              721          736
AAV1   (721) YTEPRPIGTRYLTRPL
AAV6   (721) YTEPRPIGTRYLTRPL
```

Figure 13

SEQUENCE LISTING

```
<160> NUMBER OF SEQ ID NOS: 6

<210> SEQ ID NO 1
<211> LENGTH: 585
<212> TYPE: PRT
<213> ORGANISM: Homo sapiens

<400> SEQUENCE: 1

Met Thr Pro Pro Arg Leu Phe Trp Val Trp Leu Leu Val Ala Gly Thr
1               5                  10                  15

Gln Gly Val Asn Asp Gly Asp Met Arg Leu Ala Asp Gly Gly Ala Thr
            20                  25                  30

Asn Gln Gly Arg Val Glu Ile Phe Tyr Arg Gly Gln Trp Gly Thr Val
        35                  40                  45

Cys Asp Asn Leu Trp Asp Leu Thr Asp Ala Ser Val Val Cys Arg Ala
    50                  55                  60

Leu Gly Phe Glu Asn Ala Thr Gln Ala Leu Gly Arg Ala Ala Phe Gly
65                  70                  75                  80

Gln Gly Ser Gly Pro Ile Met Leu Asp Glu Val Gln Cys Thr Gly Thr
                85                  90                  95

Glu Ala Ser Leu Ala Asp Cys Lys Ser Leu Gly Trp Leu Lys Ser Asn
            100                 105                 110

Cys Arg His Glu Arg Asp Ala Gly Val Val Cys Thr Asn Glu Thr Arg
        115                 120                 125

Ser Thr His Thr Leu Asp Leu Ser Arg Glu Leu Ser Glu Ala Leu Gly
    130                 135                 140

Gln Ile Phe Asp Ser Gln Arg Gly Cys Asp Leu Ser Ile Ser Val Asn
145                 150                 155                 160

Val Gln Gly Glu Asp Ala Leu Gly Phe Cys Gly His Thr Val Ile Leu
                165                 170                 175

Thr Ala Asn Leu Glu Ala Gln Ala Leu Trp Lys Glu Pro Gly Ser Asn
            180                 185                 190

Val Thr Met Ser Val Asp Ala Glu Cys Val Pro Met Val Arg Asp Leu
        195                 200                 205
```

```
Leu Arg Tyr Phe Tyr Ser Arg Arg Ile Asp Ile Thr Leu Ser Ser Val
    210                 215                 220

Lys Cys Phe His Lys Leu Ala Ser Ala Tyr Gly Ala Arg Gln Leu Gln
225                 230                 235                 240

Gly Tyr Cys Ala Ser Leu Phe Ala Ile Leu Leu Pro Gln Asp Pro Ser
                245                 250                 255

Phe Gln Met Pro Leu Asp Leu Tyr Ala Tyr Ala Val Ala Thr Gly Asp
            260                 265                 270

Ala Leu Leu Glu Lys Leu Cys Leu Gln Phe Leu Ala Trp Asn Phe Glu
        275                 280                 285

Ala Leu Thr Gln Ala Glu Ala Trp Pro Ser Val Pro Thr Asp Leu Leu
    290                 295                 300

Gln Leu Leu Pro Arg Ser Asp Leu Ala Val Pro Ser Glu Leu Ala
305                 310                 315                 320

Leu Leu Lys Ala Val Asp Thr Trp Ser Trp Gly Glu Arg Ala Ser His
                325                 330                 335

Glu Glu Val Glu Gly Leu Val Glu Lys Ile Arg Phe Pro Met Met Leu
            340                 345                 350

Pro Glu Glu Leu Phe Glu Leu Gln Phe Asn Leu Ser Leu Tyr Trp Ser
        355                 360                 365

His Glu Ala Leu Phe Gln Lys Lys Thr Leu Gln Ala Leu Glu Phe His
    370                 375                 380

Thr Val Pro Phe Gln Leu Leu Ala Arg Tyr Lys Gly Leu Asn Leu Thr
385                 390                 395                 400

Glu Asp Thr Tyr Lys Pro Arg Ile Tyr Thr Ser Pro Thr Trp Ser Ala
                405                 410                 415

Phe Val Thr Asp Ser Ser Trp Ser Ala Arg Lys Ser Gln Leu Val Tyr
            420                 425                 430

Gln Ser Arg Arg Gly Pro Leu Val Lys Tyr Ser Ser Asp Tyr Phe Gln
        435                 440                 445

Ala Pro Ser Asp Tyr Arg Tyr Tyr Pro Tyr Gln Ser Phe Gln Thr Pro
    450                 455                 460

Gln His Pro Ser Phe Leu Phe Gln Asp Lys Arg Val Ser Trp Ser Leu
465                 470                 475                 480

Val Tyr Leu Pro Thr Ile Gln Ser Cys Trp Asn Tyr Gly Phe Ser Cys
                485                 490                 495

Ser Ser Asp Glu Leu Pro Val Leu Gly Leu Thr Lys Ser Gly Gly Ser
            500                 505                 510

Asp Arg Thr Ile Ala Tyr Glu Asn Lys Ala Leu Met Leu Cys Glu Gly
        515                 520                 525

Leu Phe Val Ala Asp Val Thr Asp Phe Glu Gly Trp Lys Ala Ala Ile
    530                 535                 540

Pro Ser Ala Leu Asp Thr Asn Ser Ser Lys Ser Thr Ser Ser Phe Pro
545                 550                 555                 560

Cys Pro Ala Gly His Phe Asn Gly Phe Arg Thr Val Ile Arg Pro Phe
                565                 570                 575

Tyr Leu Thr Asn Ser Ser Gly Val Asp
            580                 585

<210> SEQ ID NO 2
<211> LENGTH: 559
<212> TYPE: PRT
<213> ORGANISM: Homo sapiens
```

```
<400> SEQUENCE: 2

Met Ala Leu Pro Leu Val Leu Trp Met Cys Leu Leu Val Ala Gly Thr
1               5                   10                  15

Gln Gly Val Lys Asp Gly Asp Met Arg Leu Ala Asn Gly Asp Thr Ala
            20                  25                  30

Asn Glu Gly Arg Val Glu Ile Phe Tyr Ser Gly Arg Trp Gly Thr Val
        35                  40                  45

Cys Asp Asn Leu Trp Asp Leu Met Asp Ala Ser Val Val Cys Arg Ala
    50                  55                  60

Leu Gly Phe Glu Asn Ala Thr Glu Ala Leu Gly Gly Ala Ala Phe Gly
65                  70                  75                  80

Pro Gly Lys Gly Pro Ile Met Leu Asp Glu Val Glu Cys Thr Gly Thr
                85                  90                  95

Glu Pro Ser Leu Ala Asn Cys Thr Ser Leu Gly Trp Met Lys Ser Asn
            100                 105                 110

Cys Arg His Asn Gln Asp Ala Gly Val Val Cys Ser Asn Glu Thr Arg
        115                 120                 125

Gly Ala His Thr Leu Asp Leu Ser Gly Glu Leu Pro Ala Ala Leu Glu
    130                 135                 140

Gln Ile Phe Asp Ser Gln Arg Gly Cys Asp Leu Ser Ile Arg Val Lys
145                 150                 155                 160

Val Lys Asp Gln Glu Glu Gly Pro His Phe Cys Ala His Arg Leu
                165                 170                 175

Ile Leu Ala Ala Asn Pro Glu Ala Gln Ala Leu Cys Lys Ala Pro Gly
            180                 185                 190

Ser Thr Val Thr Met Glu Val Asp Ala Glu Cys Leu Pro Val Val Arg
                195                 200                 205

Asp Phe Ile Arg Tyr Leu Tyr Ser Arg Arg Leu Asp Ile Ser Leu Thr
    210                 215                 220

Ser Val Lys Cys Phe His Lys Leu Ala Ser Ala Tyr Glu Ala Gln Gln
225                 230                 235                 240

Leu Gln Ser Phe Cys Ala Ser Leu Phe Ala Ile Leu Leu Pro Glu Asp
                245                 250                 255

Pro Ser Phe Gln Ala Pro Leu Asp Leu Tyr Ala Tyr Ala Leu Ala Thr
            260                 265                 270

Gln Asp Pro Val Leu Glu Glu Leu Cys Val Gln Phe Leu Ala Trp Asn
        275                 280                 285

Phe Glu Gly Leu Thr Gln Ala Thr Ala Trp Pro Arg Val Pro Thr Ala
    290                 295                 300

Leu Leu Gln Leu Leu Leu Ser Arg Ser Glu Leu Ala Val Pro Ser Glu
305                 310                 315                 320

Leu Ala Leu Leu Thr Ala Leu Asp Val Trp Ser Gln Glu Arg Arg Pro
                325                 330                 335

Ser His Gly Glu Val Ala Arg Leu Val Asp Lys Val Arg Phe Pro Met
            340                 345                 350

Met Leu Pro Glu His Leu Phe Glu Leu Gln Phe Asn Leu Ser Leu Tyr
        355                 360                 365

Trp Ser His Glu Ala Leu Phe Gln Lys Lys Ile Leu Gln Ala Leu Glu
    370                 375                 380

Phe His Thr Val Pro Phe Arg Leu Leu Ala Gln His Arg Gly Leu Asn
385                 390                 395                 400

Leu Thr Glu Asp Ala Tyr Gln Pro Arg Leu Tyr Thr Ser Pro Thr Trp
                405                 410                 415
```

```
Ser Ala Ser Val Ser Arg Ser Ser Arg Tyr Trp Asn Tyr Pro Tyr
            420                 425                 430

Gln Ser Phe Gln Thr Pro Gln His Pro Ser Phe Leu Phe Gln Asn Lys
            435                 440                 445

Tyr Ile Ser Trp Ser Leu Val Tyr Leu Pro Thr Val Gln Ser Cys Trp
450                 455                 460

Asn Tyr Gly Phe Ser Cys Ser Ser Asp Glu Val Pro Leu Leu Gly Leu
465                 470                 475                 480

Ser Lys Ser Asp Tyr Ser Asp Pro Thr Ile Gly Tyr Glu Asn Lys Ala
            485                 490                 495

Leu Met Arg Cys Gly Gly Arg Phe Val Ala Asp Val Thr Asp Phe Glu
            500                 505                 510

Gly Gln Lys Ala Leu Ile Pro Ser Ala Leu Gly Thr Asn Ser Ser Arg
            515                 520                 525

Arg Pro Ser Leu Phe Pro Cys Leu Gly Gly Ser Phe Ser Ser Phe Gln
            530                 535                 540

Val Val Ile Arg Pro Phe Tyr Leu Thr Asn Ser Ser Asp Val Asp
545                 550                 555

<210> SEQ ID NO 3
<211> LENGTH: 577
<212> TYPE: PRT
<213> ORGANISM: Mus musculus

<400> SEQUENCE: 3

Met Ala Leu Leu Trp Leu Leu Ser Val Phe Leu Leu Val Pro Gly Thr
1               5                   10                  15

Gln Gly Thr Glu Asp Gly Asp Met Arg Leu Val Asn Gly Ala Ser Ala
            20                  25                  30

Asn Glu Gly Arg Val Glu Ile Phe Tyr Arg Gly Arg Trp Gly Thr Val
            35                  40                  45

Cys Asp Asn Leu Trp Asn Leu Leu Asp Ala His Val Val Cys Arg Ala
50                  55                  60

Leu Gly Tyr Glu Asn Ala Thr Gln Ala Leu Gly Arg Ala Ala Phe Gly
65                  70                  75                  80

Pro Gly Lys Gly Pro Ile Met Leu Asp Glu Val Glu Cys Thr Gly Thr
            85                  90                  95

Glu Ser Ser Leu Ala Ser Cys Arg Ser Leu Gly Trp Met Val Ser Arg
            100                 105                 110

Cys Gly His Glu Lys Asp Ala Gly Val Val Cys Ser Asn Asp Thr Thr
            115                 120                 125

Gly Leu His Ile Leu Asp Leu Ser Gly Glu Leu Ser Asp Ala Leu Gly
130                 135                 140

Gln Ile Phe Asp Ser Gln Gln Gly Cys Asp Leu Phe Ile Gln Val Thr
145                 150                 155                 160

Gly Gln Gly Tyr Glu Asp Leu Ser Leu Cys Ala His Thr Leu Ile Leu
            165                 170                 175

Arg Thr Asn Pro Glu Ala Gln Ala Leu Trp Gln Val Val Gly Ser Ser
            180                 185                 190

Val Ile Met Arg Val Asp Ala Glu Cys Met Pro Val Val Arg Asp Phe
            195                 200                 205

Leu Arg Tyr Phe Tyr Ser Arg Arg Ile Glu Val Ser Met Ser Ser Val
210                 215                 220

Lys Cys Leu His Lys Leu Ala Ser Ala Tyr Gly Ala Thr Glu Leu Gln
```

```
            225                 230                 235                 240

Asp Tyr Cys Gly Arg Leu Phe Ala Thr Leu Leu Pro Gln Asp Pro Thr
            245                 250                 255

Phe His Thr Pro Leu Asp Leu Tyr Ala Tyr Ala Arg Ala Thr Gly Asp
            260                 265                 270

Ser Met Leu Glu Asp Leu Cys Val Gln Phe Leu Ala Trp Asn Phe Glu
            275                 280                 285

Pro Leu Thr Gln Ser Glu Ser Trp Ser Ala Val Pro Thr Thr Leu Ile
            290                 295                 300

Gln Ala Leu Leu Pro Lys Ser Glu Leu Ala Val Ser Ser Glu Leu Asp
305                 310                 315                 320

Leu Leu Lys Ala Val Asp Gln Trp Ser Thr Glu Thr Ile Ala Ser His
            325                 330                 335

Glu Asp Ile Glu Arg Leu Val Glu Gln Val Arg Phe Pro Met Met Leu
            340                 345                 350

Pro Gln Glu Leu Phe Glu Leu Gln Phe Asn Leu Ser Leu Tyr Gln Asp
            355                 360                 365

His Gln Ala Leu Phe Gln Arg Lys Thr Met Gln Ala Leu Glu Phe His
            370                 375                 380

Thr Val Pro Val Glu Val Leu Ala Lys Tyr Lys Gly Leu Asn Leu Thr
385                 390                 395                 400

Glu Asp Thr Tyr Lys Pro Arg Leu Tyr Thr Ser Ser Thr Trp Ser Ser
            405                 410                 415

Leu Val Met Ala Ser Thr Trp Arg Ala Gln Arg Tyr Glu Tyr Asn Arg
            420                 425                 430

Tyr Asn Gln Leu Tyr Thr Tyr Gly Tyr Gly Ser Val Ala Arg Tyr Asn
            435                 440                 445

Ser Tyr Gln Ser Phe Gln Thr Pro Gln His Pro Ser Phe Leu Phe Lys
            450                 455                 460

Asp Lys Gln Ile Ser Trp Ser Ala Thr Tyr Leu Pro Thr Met Gln Ser
465                 470                 475                 480

Cys Trp Asn Tyr Gly Phe Ser Cys Thr Ser Asn Glu Leu Pro Val Leu
            485                 490                 495

Gly Leu Thr Thr Ser Ser Tyr Ser Asn Pro Thr Ile Gly Tyr Glu Asn
            500                 505                 510

Arg Val Leu Ile Leu Cys Gly Gly Tyr Ser Val Val Asp Val Thr Ser
            515                 520                 525

Phe Glu Gly Ser Lys Ala Pro Ile Pro Thr Ala Leu Asp Thr Asn Ser
            530                 535                 540

Ser Lys Thr Pro Ser Leu Phe Pro Cys Ala Ser Gly Ala Phe Ser Ser
545                 550                 555                 560

Phe Arg Val Val Ile Arg Pro Phe Tyr Leu Thr Asn Ser Thr Asp Met
            565                 570                 575

Val

<210> SEQ ID NO 4
<211> LENGTH: 736
<212> TYPE: PRT
<213> ORGANISM: adeno-associated virus 6

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
```

```
            20                  25                  30
Lys Ala Asn Gln Gln Lys Gln Asp Asp Gly Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
            130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445
```

```
Thr Gln Asn Gln Ser Gly Ser Ala Gln Asn Lys Asp Leu Leu Phe Ser
        450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
                580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 5
<211> LENGTH: 736
<212> TYPE: PRT
<213> ORGANISM: artificial
<220> FEATURE:
<223> OTHER INFORMATION: adeno-associated virus 6 VP1 protein - K531E
      substitution

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
```

```
                65                  70                  75                  80
            Gln Gln Leu Lys Ala Gly Asp Asn Pro Tyr Leu Arg Tyr Asn His Ala
                            85                  90                  95
            Asp Ala Glu Phe Gln Glu Arg Leu Gln Glu Asp Thr Ser Phe Gly Gly
                        100                 105                 110
            Asn Leu Gly Arg Ala Val Phe Gln Ala Lys Lys Arg Val Leu Glu Pro
                        115                 120                 125
            Phe Gly Leu Val Glu Gly Ala Lys Thr Ala Pro Gly Lys Lys Arg
                130                 135                 140
            Pro Val Glu Gln Ser Pro Gln Glu Pro Asp Ser Ser Gly Ile Gly
            145                 150                 155                 160
            Lys Thr Gly Gln Gln Pro Ala Lys Lys Arg Leu Asn Phe Gly Gln Thr
                            165                 170                 175
            Gly Asp Ser Glu Ser Val Pro Asp Pro Gln Pro Leu Gly Glu Pro Pro
                        180                 185                 190
            Ala Thr Pro Ala Ala Val Gly Pro Thr Thr Met Ala Ser Gly Gly Gly
                        195                 200                 205
            Ala Pro Met Ala Asp Asn Asn Glu Gly Ala Asp Gly Val Gly Asn Ala
                        210                 215                 220
            Ser Gly Asn Trp His Cys Asp Ser Thr Trp Leu Gly Asp Arg Val Ile
            225                 230                 235                 240
            Thr Thr Ser Thr Arg Thr Trp Ala Leu Pro Thr Tyr Asn Asn His Leu
                            245                 250                 255
            Tyr Lys Gln Ile Ser Ser Ala Ser Thr Gly Ala Ser Asn Asp Asn His
                        260                 265                 270
            Tyr Phe Gly Tyr Ser Thr Pro Trp Gly Tyr Phe Asp Phe Asn Arg Phe
                        275                 280                 285
            His Cys His Phe Ser Pro Arg Asp Trp Gln Arg Leu Ile Asn Asn Asn
                        290                 295                 300
            Trp Gly Phe Arg Pro Lys Arg Leu Asn Phe Lys Leu Phe Asn Ile Gln
            305                 310                 315                 320
            Val Lys Glu Val Thr Thr Asn Asp Gly Val Thr Thr Ile Ala Asn Asn
                            325                 330                 335
            Leu Thr Ser Thr Val Gln Val Phe Ser Asp Ser Glu Tyr Gln Leu Pro
                        340                 345                 350
            Tyr Val Leu Gly Ser Ala His Gln Gly Cys Leu Pro Pro Phe Pro Ala
                        355                 360                 365
            Asp Val Phe Met Ile Pro Gln Tyr Gly Tyr Leu Thr Leu Asn Asn Gly
                        370                 375                 380
            Ser Gln Ala Val Gly Arg Ser Ser Phe Tyr Cys Leu Glu Tyr Phe Pro
            385                 390                 395                 400
            Ser Gln Met Leu Arg Thr Gly Asn Asn Phe Thr Phe Ser Tyr Thr Phe
                            405                 410                 415
            Glu Asp Val Pro Phe His Ser Ser Tyr Ala His Ser Gln Ser Leu Asp
                        420                 425                 430
            Arg Leu Met Asn Pro Leu Ile Asp Gln Tyr Leu Tyr Tyr Leu Asn Arg
                        435                 440                 445
            Thr Gln Asn Gln Ser Gly Ser Ala Gln Asn Lys Asp Leu Leu Phe Ser
                        450                 455                 460
            Arg Gly Ser Pro Ala Gly Met Ser Val Gln Pro Lys Asn Trp Leu Pro
            465                 470                 475                 480
            Gly Pro Cys Tyr Arg Gln Gln Arg Val Ser Lys Thr Lys Thr Asp Asn
                            485                 490                 495
```

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 6
<211> LENGTH: 736
<212> TYPE: PRT
<213> ORGANISM: adeno-associated virus 1

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg

```
                130                 135                 140
Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
                195                 200                 205

Ala Pro Met Ala Asp Asn Asn Glu Gly Ala Asp Gly Val Gly Asn Ala
        210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
                275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
        450                 455                 460

Arg Gly Ser Pro Ala Gly Met Ser Val Gln Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
                515                 520                 525

Asp Asp Glu Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560
```

```
Thr Asp Glu Glu Ile Lys Ala Thr Asn Pro Val Ala Thr Glu Arg
            565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys Asn Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

METHODS OF INCREASING EFFICIENCY OF VECTOR PENETRATION OF TARGET TISSUE

This application is a National Stage Application of PCT/EP2011/054378, filed 22 Mar. 2011, which claims benefit of U.S. Provisional Ser. No. 61/316,302, filed 22 Mar. 2010 and which applications are incorporated herein by reference. To the extent appropriate, a claim of priority is made to each of the above disclosed applications.

FIELD OF THE INVENTION

The present invention relates to methods for increasing the efficiency of target tissue penetration of an adeno-associated virus (AAV) in a patient. In some aspects, the methods involve inhibiting the interaction of the serum protein galectin 3 binding protein (G3BP) with AAV. The present invention also provides methods for reducing tissue distribution of a virus, or for neutralizing a virus harbored by an organ destined for transplantation or newly transplanted, by exposing the organ or administering to the patient a composition comprising G3BP.

BACKGROUND OF INVENTION

Galectin-3 binding protein (G3BP), also known as 90-kDa Mac-2 binding protein, was initially identified and characterized in breast cancer cells and in human milk [see, Koths K. et al. (1993) J. Biol. Chem. 268:14245-14249], and is a heavily N-glycosylated secreted protein of about 90 kDa. G3BP is known to interact with Galectin-3, Galectin-1 and Galectin-7 [see, Inohara et al. (1996) Cancer Research 56:4530-4534; Tinari, N. (2001) Int J Cancer 91:167-172; Liu, F T et al. (2005) Nat Rev Cancer 5:29-41]. Further, G3BP is elevated in the serum of subpopulations of patients with various types of cancer [see, Iacobelli S. et al. (1986) Cancer Res. 46:3005-3010; Iacobelli S. et al. (1988) Breast Cancer Res. Treat. 11:19-30; Iacobelli S. et al. (1994) Br. J. Cancer 69:172-176; Scambia, G. et al. (1988) Anticancer Res. 8:761-764], and in patients infected with human immunodeficiency virus (HIV) [see, Natoli et al. (1991) J. Infect. Dis. 164:616-617; Natoli et al. (1993) J. AIDS 6:370-375; Iacobelli, S. et al. (1991) J. Infect. Dis. 164:189; Briggs, N.C. et al. (1993) AIDS Res. Hum. Retroviruses; 9:811-816; Longo, G. et al. (1993) Br. J. Haematol. 85:207-209]. G3BP also has stimulatory effects on cells of the immune system, such as NK cells and lymphokine-activated killer cells [see, Ullrich, A. et al. (1994) J. Biol. Chem. 269:18401-18407]. A role for G3BP in inhibiting the spread of viruses within a host's body, however, has not been previously described.

While the immune system is designed to fight and, ideally, inhibit the spread of viral infection, certain viruses are especially adept at evading or overcoming the immune response. Moreover, immunocompromised individuals, such as those taking immunosuppressant drugs to prevent rejection of a transplanted organ, or those infected with HIV, are particularly susceptible to viral infection. While antiviral medications are currently available for some viruses, many viruses rapidly mutate and become resistant to these drugs, and for other viruses, no such drugs are available [see, Barth R E et al. (2010), Lancet Infect Dis; 10:155-66; Marcelin A G et al. (2009), Curr Opin HIV AIDS; 4:531-537]. Therefore, new compositions and methods for preventing, delaying, or limiting the severity of viral infection in an individual are needed.

In the case of gene therapy, which is a technique for correcting a defective gene responsible for disease development by replacing or introducing mutations into the defective gene, it is actually desirable to enhance the spread of a virus (in the form of a vector) to organs and tissues. Specifically, viral vectors, such as those derived from adeno-associated virus (AAV), are commonly used to deliver a corrective gene to target tissues, and inhibiting or delaying the spread of such vectors to target tissues severely limits the efficacy of the vector. Currently, a number of vectors that would otherwise be useful for gene therapy, including AAV vectors in particular, are plagued by low efficiency, and methods for increasing their efficiency are needed.

AAV is an attractive candidate for generating viral vectors for gene therapy, because it is a small, single-stranded DNA virus that infects humans and certain other mammalian species, including dogs, but does not cause infection or elicit a strong host immune response. There are 11 known serotypes of AAV, AAV1-AAV11. AAV expresses the capsid proteins VP1, VP2 and VP3, which are involved in and are thought to be required for AAV infection of target tissues. The molecular weights of these proteins are 87, 72, and 62 kDa, respectively [Jay F T et al. (1981) PNAS; 78:2927-31]. Given the importance of capsid integrity on infectivity, all capsid proteins are likely required for infection. VP2 is especially important, as AAV capsid can only form in its presence [Ruffing et al. (1992) Journal of Virology; 66:6922-6930].

Clinical trials evaluating the safety and efficacy of AAV-vector based gene therapy for a broad variety of conditions are currently underway. These conditions include, for example, Pompe disease (caused by an acid alpha-glucosidase deficiency), inflammatory arthritis, Lebers Congenital Amaurosis (caused by RPE65 mutations), Canavan disease, childhood blindness (caused by mutations in RPE65), alpha 1-antitrypsin deficiency, heart failure, hemophilia, limb girdle muscular dystrophy type 2D, lipoprotein lipase deficiency, cystic fibrosis, Parkinson's disease, Duchenne muscular dystrophy, late infantile neuronal ceroid lipofuscinosis, Alzheimer's disease, and cutaneous B cell lymphoma [see, Journal of Gene Medicine website at http://www.wiley.co.uk/genetherapy/clinical/; http://www.abedia.com/wiley/images/0912vectors.jpg; Rodino-Klapac et al, Neurology (2008); 71:240-247; Towne et al, Gene Ther. (2010); 17: 141-146].

For effective use in gene therapy to treat conditions such as those described above, an AAV vector must achieve systemic distribution throughout target tissues (i.e., "tissue distribution"). One disadvantage of using AAV vectors for gene therapy is that many individuals are already seropositive for AAV. For instance, this value varies from 5% for AAV5 to 60% for AAV2 (these values are known for AAV1, 2, 5, 6, 8, 9) [see, Boutin et al., Hum Gene Ther. (2010) January 22. [Epub ahead of print]]. Serum antibodies in this population bind to and sequester AAV in the blood. The resultant antibody-AAV complexes are cleared by the liver, thereby preventing systemic distribution of the vector.

Even in gene therapy patients who are seronegative for AAV, however, efficiency of AAV penetration in target tissues is low, and high amounts of AAV vector must be administered to the patient in order for the dose of AAV to effectively achieve systemic distribution, including distribution into target tissues. The requirement for high concentrations of AAV vector poses a significant disadvantage for its use in gene therapy, since vector overloading can be toxic under certain circumstances. Furthermore, such high titres of vector can be difficult to produce. (See, Virag et al., Hum Gene Ther. (2009) 20:807-817).

As described above, there remains a need to identify methods and compositions for increasing the efficiency of AAV penetration into target tissues and to identify methods and compositions for inhibiting the spread of harmful viral infections. The present invention provides such methods and compositions.

SUMMARY OF INVENTION

In one embodiment, the present invention relates to a method for increasing the efficiency of target tissue penetration of an AAV vector in a patient by abrogating the galectin 3 binding protein (G3BP)-mediated reduction of tissue penetration. Exemplary methods include depleting or neutralizing G3BP protein by, for example, chromatography, plasmapheresis, affinity columns, G3BP depleting antibodies, G3BP neutralizing antibodies, and G3BP inhibitors. Each of these methods are applied to reduce the serum concentration of G3BP to a concentration of less than about 5 µg/ml, more preferably to less than 3 µg/ml, less than 2.5 µg/ml, and more preferably to less than about 1 µg/ml. AAV vectors of the present invention can be selected from the group consisting of AAV1-, AAV-5, AAV-6, and AAV-8. These AAV vectors can be structurally modified such that that G3BP no longer interacts with the modified AAV vector. For example, an AAV vector can be modified such that its capsid is replaced with the capsid of AAV9, which does not interact with G3BP. Because AAV1 captures less G3BP compared to AAV6 (FIG. 3), AAV vector can also be modified by replacement of at least one, in particular at least two, of the 6 amino acids that are different between AAV1 and AAV6. All six possible substitutions (F129L; D418E; K531E; L584F; V598A; H642N) are potential sites for modification of the capsid in order to diminish G3BP binding to the thus modified AAV6 vector to the level of AAV1 or less. In this regard, the K531E substitution is of special interest since it changes charge distribution on the surface of the AAV6 vector.

In another embodiment, the present invention relates to a method for reducing tissue distribution of a virus in a patient by administering a composition comprising G3BP in an effective amount for retaining the virus in serum. A composition comprising G3BP for use in a method for reducing tissue distribution of a virus in a patient is also an object of the invention. Targeted viruses include, but are not limited to, influenza virus, hepatitis C virus (HCV), hepatitis B virus (HBV), adenovirus, herpes simplex virus, varicell zoster virus, cytomegalovirus, Epstein-Bar virus (EBV), measles virus, rubeola virus, respiratory syncytial virus, rotavirus, metapneumovirus, norovirus, sapovirus, mumps virus, coxsackie virus, parovirus, lyssavirus, or human immunodeficiency virus. The composition comprising G3BP can be administered, for example, intravenously at a therapeutically effective dose. In other embodiments, the composition comprising G3BP can be co-administered with at least one additional composition. Such additional compositions can include, for example, acyclovir, interferon-ribaviri, compositions for anti-retroviral therapy, and compositions for specific or non-specific immunoglobulin treatment adapted to the specific virus in question. In certain embodiments, the patient to whom the composition comprising G3BP is administered is an organ transplant patient. Such patients can, for example, be administered the composition comprising G3BP prior to, at the time of, or after organ transplantation. In some cases, a patient may have been infected by a virus introduced by a transplanted organ.

In yet another embodiment, the present invention relates to a method for combating a virus harbored by an organ destined for transplantation into a patient in vitro, the method comprising exposing the organ to G3BP in vitro in an effective amount for reducing the ability of the virus to achieve tissue distribution after transplantation into the patient. Suitable G3BP for use in such methods include recombinant G3BP, isolated G3BP, or a G3BP mimetic agent. G3BP can be administered to an organ destined for transplantation by, for example, hypothermic or normothermic perfusion.

In yet another embodiment, the present invention relates to a method for limiting the titer or load of a virus that would be achieved in a patient by administering a composition comprising G3BP in an effective amount for limiting the titer or load of the virus in serum. The invention thus also relates to a composition comprising G3BP for use in a method for limiting the titer or load of a virus in a patient. Suitable G3BP for use in such methods include recombinant G3BP, isolated G3BP, or G3BP mimetic agent. In related methods, G3BP can be conjugated to an anti-viral agent or anti-viral compound.

In yet another embodiment, the present invention relates to a method for reducing tissue distribution of a virus in a patient by administering a composition comprising a protein with a scavenger receptor cysteine-rich domain in an effective amount for retaining the virus in serum. In yet another embodiment, the invention relates to a method for reducing tissue distribution of a virus in a patient by administering a composition comprising murine CRP protein.

These and other embodiments, features and advantages of the disclosure will become apparent from the detailed description and the appended claims set forth herein below.

BRIEF DESCRIPTION OF THE DRAWINGS

(FIG. 6A) 6×10E11 rAAV-6 in PBS; 6×10E11 rAAV-6 pre-incubated with hu-G3BP (20 μg/ml); 6×10E11 rAAV-6 in PBS followed by an injection of 20 μg of hu-G3BP; injection of 20 μg of G3BP followed by an injection of 6×10E11 rAAV-6. (FIG. 6B) Serum levels of MuSEAP (ng/ml) two weeks after systemic injection of 10E11 rAAV-9 MuSEAP vectors in PBS (left) or mixed with 20 μg/ml hu-G3BP (right). (FIG. 6C) MuSEAP levels following single intramuscular injections of 5×10E9 rAAV-6 MuSEAP alone and in combination with 20 μg/ml hu-G3BP; similar experiments were carried out with 5×10E9 rAAV-8, 5×10E9 rAAV-7 and 10E9 rAAV-9 MuSEAP. At least three mice were used in each assay.

FIG. 13 Alignment of VP1 proteins of AAV1 and AAV6. AAV1 binds less G3BP compared to AAV6 (FIG. 3) and VP1 proteins of these serotypes differ by only six amino acids. All six (F129L; D418E; K531E; L584F; V598A; H642N) are potential sites for modification of the capsid in order to diminish G3BP binding to the level of AAV1 or less.

Figure 1:
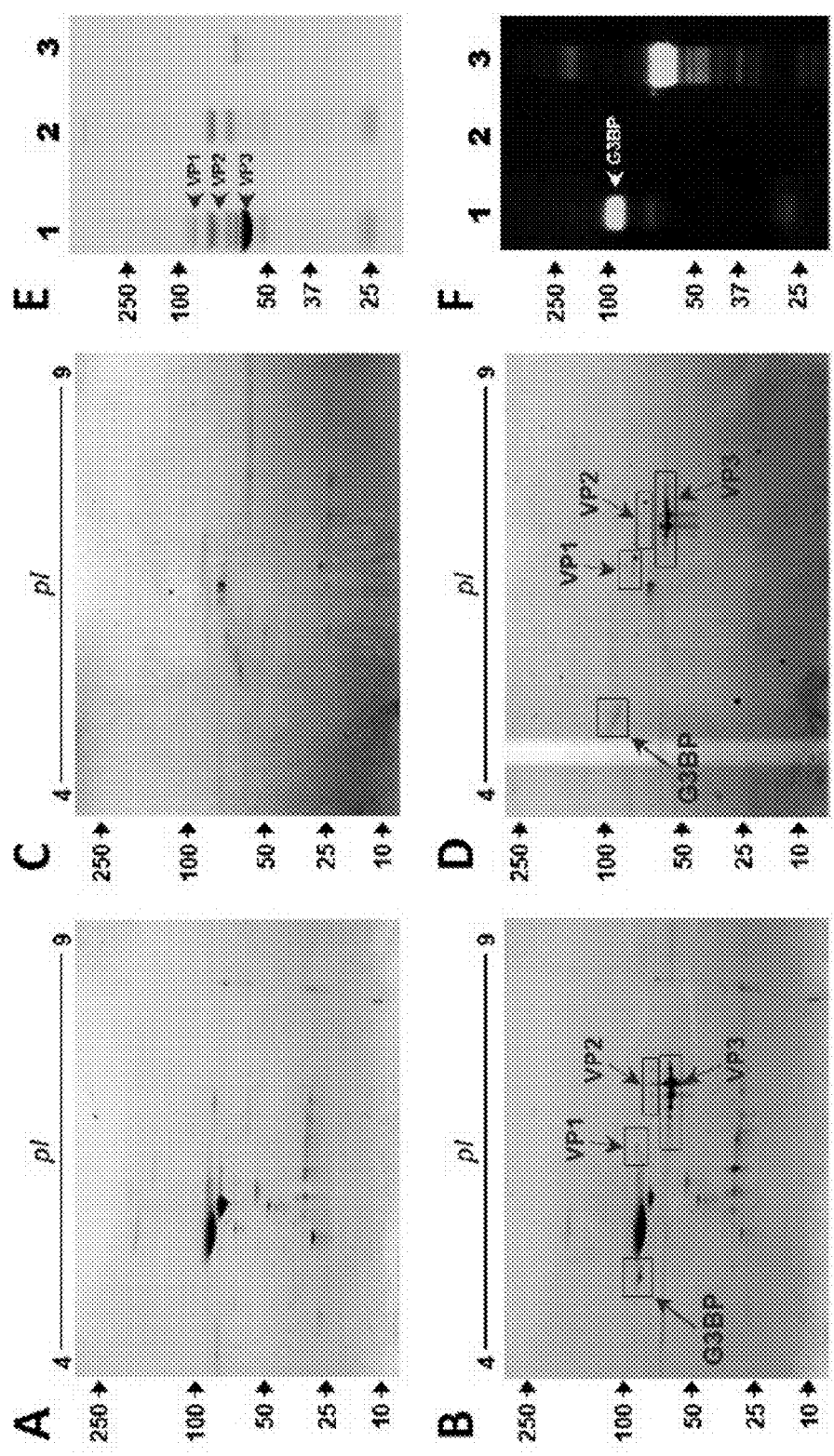
FIGS. 1A and 1B are images of Coomassie-stained two-dimensional (2D) polyacrylamide gels of dog serum proteins recovered by ultracentrifugation in the absence (FIG. 1A) or presence (FIG. 1B) of rAAV-6. Arrows in FIG. 1B indicate G3BP and VP1-3.
FIGS. 1C and 1D are images of Coomassie-stained 2D polyacrylamide gels of human serum proteins recovered with AVB-Sepharose immune-affinity beads, with beads alone (FIG. 1C) or beads with rAAV-6 (FIG. 1D).
FIG. 1E is an image of a Coomassie-stained gel of protein extracts from human serum recovered with AVB immune-affinity beads with rAAV-6 or beads alone (lanes 1 and 2), or purified non-glycosylated G3BP (lane 3).
FIG. 1F is the corresponding Western blot for G3BP for the experiment in FIG. 1E.

Lane 3: unfractionated human serum; Lane 4: recombinant CRP (100 ng) stabilized with BSA.

DETAILED DESCRIPTION OF THE INVENTION

It is presently discovered that the serum glycoprotein, galectin-3 binding protein (G3BP), previously known only to bind to its natural ligands such as Galectin-1, -3 and -7, also interacts with adeno-associated virus (AAV). Further, it is discovered that the interaction of G3BP with AAV results in reduced viral penetration of organs and tissues.

As used herein the terms "reduced," "reduction of," and other grammatical variants of these terms, in the context of, e.g., "reduced/reduction of viral penetration of a target tissue," or "reducing the spread/tissue distribution of a virus", mean that the viral penetration of the target tissue is decreased or entirely abolished, and/or delayed (i.e., it takes longer than normal for the virus to penetrate the target tissue). For example, a virus that interacts with G3BP in the serum is retained in the serum and prevented or delayed from spreading to target tissues, such as organs, of the patient. This G3BP-interacting virus will have reduced tissue distribution. On the other hand, a viral vector uninhibited by G3BP (through either neutralization or depletion/removal of G3BP from the serum) has greater tissue and organ penetration including in the target organ, e.g., the target of a gene therapy treatment.

As used herein, the term "AAV" can mean the virus itself or a viral vector derived from the virus and optionally incorporating an exogenous gene or other exogenous nucleotide sequence. Certain AAV vectors are commercially available, e.g., from ReGenX Biosciences, LLC (Washington, D.C.) or are publically available, e.g. Genethon (EVRY, France).

In conjunction with this discovery, the present invention provides methods for enhancing the spreading of AAV to target organs and tissues by abrogating G3BP-mediated reduction of AAV tissue distribution.

As used herein, the term "abrogating," and its grammatical variants, means to abolish or reduce.

In certain embodiments, G3BP-mediated reduction of AAV tissue distribution is abrogated by removing G3BP from the serum in vivo or ex vivo, or by removing it from the organ or tissue or other G3BP-containing sample being treated in vitro. In other embodiments, G3BP-mediated reduction of AAV tissue distribution is abrogated by preventing or limiting G3BP interaction with AAV (e.g., using a neutralizing antibody of the invention).

The present invention also provides methods for treating systemic viral infections resulting from other infective viruses, such as those associated with organ transplantation (e.g., HCV, HBV, adenovirus) and also infective viruses such as influenza virus, and others.

It is anticipated that the present invention will apply to a number of viruses since it is highly unlikely that such a mechanism has developed for AAV only. The present inventors have developed and plan to test experimentally whether:
(i) G3BP interacts in a similar manner with other viruses;
ii) The scavenger receptor cysteine-rich domain of G3BP [Hohenester et al. (1999), Nat Struct Biol. 6:228-232] is the domain conferring antiviral properties and in this case other proteins carrying this domain could provide an anti-viral serum buffer;
iii) Different proteins with completely different domains are capable of acting as an anti-viral serum buffer. For example, G3BP is not active in this manner in the mouse. This role is played instead by C-reactive protein.

In any event, the general principle that a serum protein acts as a buffer for a viral infection is believed to be previously unrecognized as a component of anti-viral defense. The present inventors also discovered that G3BP acts on different strains of AAV. Extrapolation of the same principle to other viruses is plausible.

In a specific embodiment, the invention provides a method for increasing the efficiency of target tissue penetration of AAV in a patient in need thereof, which method comprises abrogating G3BP-mediated reduction of AAV tissue penetration.

The invention also relates to a method for increasing virus-mediated gene delivery in a subject, which method comprises neutralizing G3BP in said subject prior to or during said gene delivery. In a specific variant, the virus-mediated gene delivery is an AAV-mediated gene delivery, in particular with AAV-1, -5, -6 or -8, most particularly AAV-6.

The invention also relates to a composition comprising a G3BP-neutralizing compound for use in a method of virus-mediated gene delivery in a subject. In a specific variant, the virus-mediated gene delivery is an AAV-mediated gene delivery, in particular with AAV-1, -5, -6 or -8, most particularly AAV-6.

The invention also relates to a composition comprising a viral gene delivery vector and a G3BP-neutralizing compound, for combined, separate or sequential administration to a subject.

In another embodiment, the invention relates to G3BP for use in reducing virus load in a subject.

In another specific embodiment, the invention provides a method for reducing tissue distribution of a virus in a patient, which method comprises administering to a patient in need thereof a composition comprising G3BP in an effective amount for retaining the virus in the serum. Such an embodiment would be directed to reducing the spread of viral infections to tissues or organs in a subject infected with a pathogenic virus and having a viral load in the serum, or in a subject who is at risk for becoming infected with a pathogenic virus and acquiring a viral load in the serum (e.g. an organ transplant recipient). Thus, in a specific embodiment, the subject is an organ transplant recipient, who is going to receive, is receiving, or has very recently received an organ.

In yet another specific embodiment, the invention provides a method for neutralizing a virus harbored by an organ destined for transplantation into a subject, which method comprises exposing said organ to G3BP in vitro or ex vivo in an effective amount for inhibiting the ability of said virus to spread to the subject's tissues and organs upon transplantation into the subject.

In yet another specific embodiment, the invention provides a method for neutralizing a virus present in the serum of a patient, which method comprises administering to a patient in need thereof a composition comprising a protein containing a scavenger receptor cysteine-rich domain [Hohenester et al. (1999), Nat Struct Biol. 6:228-232], such as, for example, G3BP or a protein like murine CRP.

In yet another specific embodiment, the invention provides a method for limiting the titer or load of a virus that would be achieved in a patient, which method comprises administering to a patient in need thereof a composition comprising galectin 3 binding protein (G3BP) in an effective amount for decreasing the titer of said virus in serum.

In yet another specific embodiment, the invention provides a method for identifying serum proteins able to decrease a virus transduction efficiency, comprising the steps of:
1) in a serum sample of a subject seronegative for said virus, screening for protein(s) interacting with said virus, and selecting said protein(s)
2) evaluating said protein ability to decrease the transduction efficiency of said virus, and selecting the protein(s) that are capable of decreasing said transduction efficiency.

Representative proteins that could be identified are those that decrease the transduction efficiency of adeno-associated virus, influenza virus, hepatitis C virus (HCV), hepatits B virus (HBV), adenovirus, various herpes simplex virus strains, varicella zoster virus, cytomegalovirus, Epstein-Bar virus (EBV), measles virus, rubeola virus, respiratory syncytial virus, rotavirus, metapneumovirus, norovirus, sapovirus, mumps virus, coxsackie virus, parvovirus, lyssavirus, or human immunodeficiency virus (HIV).

In another specific embodiment, the invention provides a method for identifying compounds that can increase the efficiency of a gene therapy viral vector derived from a virus, said method comprising the step of screening for compounds that decrease the interaction of said virus with a serum protein able to decrease the virus efficiency. In a particular embodiment, the serum protein has been identified by the method described in the preceding paragraph. In another specific embodiment, the method for identifying compounds that can increase the efficiency of a gene therapy viral vector first comprise as a first step the implementation of the method for identifying serum proteins able to decrease a virus efficiency of the preceding paragraph. In a specific embodiment, the protein is G3BP and the virus is an AAV, in particular an AAV-1, -5, -6 or -8 vector. As such, the invention also provides a method for identifying G3BP neutralizing compounds, said compound being useful for increasing the transduction efficiency of an AAV, in particular an AAV-1, -5, -6 or -8 vector, most preferably of an AAV6 vector.

In yet another specific embodiment, the invention provides a mutated AAV6 VP protein, comprising a mutation in said protein, the mutation decreasing the interaction between an AAV6 vector comprising said modified VP protein and G3BP without decreasing (or only mildly decreasing) said AAV6 vector capacity to transduce target cells. "Mildly decreasing" the transduction capacity of the AAV6 vector denotes a decrease in the transduction efficiency of the vector comprising the mutated VP protein, by comparison to the vector comprising the non mutated VP protein, as measured in a reporter assay, of less than 50%, preferably less than 60%, less than 70%, less than 80%, less than 90%, most preferably less than 95%. In a particular embodiment, the VP protein is an AAV6 VP protein comprising at least one, in particular at least two, but not all the F129L, D418E, K531E, L584F, V598A and H642N mutations in the sequence shown in SEQ ID NO:4. In yet another embodiment, the invention provides an AAV6 recombinant vector comprising such a mutated VP protein, in particular a VP protein comprising the K531E mutation (SEQ ID NO:5). The results presented herein show that AAV1 is not as efficiently inactivated by G3BP as AAV6. A mutation in AAV6 VP protein in at least one, in particular at least two, but not all of the amino acid positions differing from the corresponding amino acid positions in AAV1 (see FIG. 13: sequence alignment of AAV6 AND AAV1 VP proteins) is thus believed to result in a decrease in the binding of the resulting modified AAV6 vector to G3BP. Of course, these and other mutations of the VP protein that are likely to be efficient for decreasing the binding of AAV6 to G3BP without impacting the transduction efficiency and tissue specificity of said AAV6 are part of the invention. According to a specific embodiment, the invention relates to an AAV6 vector comprising an AAV6 protein modified between the amino acid positions 525-540 as shown in SEQ ID NO:4, this region being likely to be important for interaction with G3BP given the importance of the lysine in position 531.

In another specific embodiment, the invention provides a method of gene therapy of a subject, comprising administering to said subject an efficient amount of a recombinant AAV6 vector comprising a therapeutic exogenous polynucleotide or oligonucleotide, wherein said vector comprises a mutated AAV6 VP protein that presents a decreased binding to G3BP in comparison to the non mutated form of the VP protein. In a particular embodiment, said mutation is K531E. Wu et al. have shown that this mutation might be important for tissue distribution of AAV6 but the finding that AAVs, in particular AAV6, can bind G3BP is believed to be unrecognized in the art.

In another specific embodiment, the invention provides a method for increasing AAV6 virus-mediated delivery of a therapeutic exogenous polynucleotide or oligonucleotide in a tissue targeted by AAV6, comprising administering to a subject in need thereof an effective amount of a recombinant AAV6 vector comprising a therapeutic gene, wherein said vector comprises a mutated AAV6 VP protein that present a decreased binding to G3BP in comparison to the non mutated form of the VP protein. In a particular embodiment, said mutation is K531E. AAV6 has been shown to be able to target various tissues including, for example, muscle, cochlea (Kilpratick et al., 2011), dendritic cells (Ussher et al., 2010), osteoblasts (Jiang et al., 2010; Halbert et al. 2010) and the retina (Klimczak et al., 2009).

DEFINITIONS

As used herein, the terms "target tissue penetration" and "tissue distribution" of a virus or viral vector mean entry and residence by the virus or vector in the target tissue or tissues, such as an organ. The "efficiency" of tissue penetration/distribution may be measured by quantifying viral load in the target tissue and dividing this by the starting viral load, and comparing this ratio to a standard or control.

As used herein, the term "retaining the virus in the serum" means that the virus is prevented, either partially or fully, and/or delayed from leaving the circulation (blood). A virus that is retained in the serum will have reduced tissue distribution.

As used herein, the term "spread to patient tissues" means that a virus from a transplanted organ or tissue achieves tissue distribution in the patient.

As used herein, the term "host," means a subject or patient infected with a virus.

As used herein the term "neutralizing a virus" means preventing or significantly reducing the ability of a virus to achieve tissue distribution in a host.

As used herein, the term "G3BP-neutralizing compound" or "G3BP inhibitor" designates any compound which can reduce the interaction between G3BP and a virus, in particular between G3BP and AAV6. The compound may be e.g., an antibody, a polypeptide or peptide, a nucleic acid, a sugar, or a small drug. Preferred G3BP-neutralizing compounds are compounds which bind to G3BP and inhibit or reduce the ability of G3BP to bind a virus, such as AAV. Other preferred G3BP-neutralizing compounds are compounds which decrease the serum concentration of G3BP, preferably down to a level of 5 µg/ml or less.

As used herein, a "G3BP neutralizing antibody" is an antibody that prevents G3BP from interacting with AAV or other virus (or in any event reduces the amount of G3BP that is available to interact with the AAV) and thereby prevents G3BP from retaining AAV or other virus in the serum, enabling it to enter the target cells. A G3BP neutralizing antibody of the invention may or may not prevent G3BP from binding to its non-viral ligands, e.g., Galectin-1, Galectin-3, and Galectin-7.

As used herein, a "G3BP depleting antibody" is an antibody that causes significant reduction or complete elimination of the serum concentration of G3BP. In a preferred embodiment, a G3BP depleting antibody of the invention reduces serum concentration of G3BP to a concentration between about 1 µg/ml and about 5 µg/ml, and more preferably, between about 1 µg/ml and about 3 µg/ml. In a specific embodiment, a G3BP depleting antibody of the invention reduces serum concentration of G3BP to a concentration below about 2.5 µg/ml.

As used herein, the term "depletion" means reduction and/or complete abolishment.

As used herein, "G3BP" refers to the full-length G3BP protein or a variant of G3BP. As used herein, "variant" in addition to its understood meaning as a term of art includes any changes in a molecule from its wild-type form. For example, alleles, fragments, mutations, deletions, substitutions with natural or analog compounds, splice variants, glycosylations, species variants, and the like. The term is not limited to any one type of change or deviation from the wild type form or "normal" molecule. A "variant" also includes a polypeptide or enzyme which has at least 60% amino acid identity as determined by BLAST or FASTA algorithms, preferably at least 75%, most preferably at least 85%, and even more preferably at least 90%, and still more preferably at least 95%, and which has the same or substantially similar properties or functions as the native or parent protein or enzyme to which it is compared, i.e., the ability to interact with AAV, in particular AAV-1, -5, -6 or -8, most particularly AAV-6, and/or other viruses disclosed herein and reducing ability of AAV and/or other viruses to achieve tissue distribution in vivo. In one embodiment of the invention, G3BP can be glycosylated. In another embodiment, G3BP can be non-glycosylated.

The term "subject" or "individual" as used herein refers to an animal, preferably a mammal (e.g., dog). In particular, the term encompasses humans.

As used herein, the term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

The terms "gene", "polynucleotide," and "oligonucleotide" are used interchangeably herein to denote an exogenous nucleotide string or sequence introduced into an rAAV vector for the purpose of repairing, skipping, replacing or silencing a defective gene or portion thereof in a host infected with the vector.

The term "exogenous polynucleotide", "exogenous oligonucleotide" or "exogenous DNA sequence" as used herein refers to a nucleic acid sequence that does not originate from the host in which it is placed. It may be identical to the host's DNA or heterologous. An example is a sequence of interest inserted into a vector. Such exogenous DNA sequences may be derived from a variety of sources including DNA, cDNA, synthetic DNA, and RNA. Such exogenous DNA sequences may comprise genomic DNA which may or may not include introns either naturally occurring or artificial. Moreover, such genomic DNA may be obtained in association with promoter regions or poly A signal sequences. The exogenous DNA sequences in the present invention can be cDNA. An exogenous DNA sequence includes without limitation any DNA sequence whose expression produces a gene product that is to be expressed in a host cell. The gene product may affect the physiology of the host cell. Exogenous DNA sequences also encompass DNA sequences that encode antisense oligonucleotides.

"Treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving the disease, i.e., causing regression of the state, disorder or condition or at least one of its clinical or subclinical symptoms.

The benefit to an individual to be treated is either statistically significant or at least perceptible to the patient or to the physician.

The compositions of the invention will typically contain an effective amount of the protein containing a scavenger receptor cysteine-rich domain (e.g G3BP) or the protein from pentraxins superfamily of proteins like murine CRP for achieving the desired effect. The term "therapeutically effective amount/dose" is used interchangeably with the "effective amount/dose" and refers to an amount of the substance that is sufficient to achieve the intended effect. For example, an effective amount of G3BP is an amount that is sufficient to inhibit or delay spread of a virus from the circulatory system to tissues and organs, and an amount that is sufficient to inhibit or delay the spread of virus from an organ to be transplanted to a recipient's circulatory system.

As used herein, the phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, "substantial" or "substantially" refers to an amount that is sufficient to produce a measurable effect.

Compositions and Uses

In a specific embodiment, the present invention provides a composition comprising one or more G3BP inhibitors. A composition comprising one or more G3BP inhibitors may be used in vitro or in vivo. Such compositions are useful, e.g., for abrogating the interaction of G3BP with a virus in the serum. In a specific embodiment, the G3BP inhibitor is effective for abrogating G3BP binding to AAV. In another specific embodiment, the G3BP inhibitor is administered directly to a patient.

G3BP inhibitors can be molecules that bind to either G3BP or to the virus whose interaction to G3BP is to be abrogated, and where said binding of the molecules interferes with, or even prevents, the interaction of G3BP with the virus. Non limiting examples are antibodies to G3BP, antibodies to the viral capsid G3BP binding domain, competing isolated viral capsid proteins and empty viral capsids.

Non-limiting examples of G3BP inhibitors include galectins such as Galectin-1, Galectin-3, Galectin-7; sugars such as β-galactoside (lactose), galactose, manose, and the like; agonistic VPs, which refer to recombinant viral particles from any AAV serotype (alone or in combination, native or chimeric forms) capable of interacting with G3BP and acting as decoys; murine C reactive protein (CRP); empty AAV caspids; fragments of G3BP capable of interacting with native G3BP; proteins or their fragments or small molecules which interact either with AAV or G3BP and prevent the interaction between AAV and G3BP (e.g., scavenger receptor cysteine-rich domain).

In another embodiment, the present invention provides a composition comprising anti-G3BP antibodies. The antibodies may be polyclonal or monoclonal and may be neutralizing antibodies or depleting antibodies. In a specific embodiment, the antibody-containing composition is administered directly to a patient.

An example of a G3BP-depleting antibody is the SP-2 monoclonal antibody, which is available from MediaPharma s.r.l. (Clinical Research Center, Chieti, Italy), or antibodies described in Laferte et al (2000), J. Cell Biochem; 77:540-559. Monoclonal antibodies can also be generated against human G3BP by methods well known in the art.

In yet another embodiment, the invention relates to a composition comprising a G3BP inhibitor in an amount effective, when the composition is administered to a human, to reduce the concentration of native G3BP in the human to less than 5 µg/ml, preferably less than 3 µg/ml, preferably less than 2.5 µg/ml, in particular less than 1 µg/ml or to undetectable levels of G3BP. In a particular embodiment, the composition is administered to reduce the concentration of native G3BP in the human to between about 1 µg/ml and 5 µg/ml, preferably between about 1 µg/ml and 3 µg/ml, most preferably between about 1 and 2.5 µg/ml.

In a specific embodiment, the present invention provides a composition comprising G3BP.

G3BP is a heavily N-glycosylated secreted protein of about 90 kDa and is known to interact with Galectin-3, Galectin-1 and Galectin-7. It is presently discovered that human and dog G3BP interacts with and binds to AAV1, AAV5, AAV6, and AAV8. The amino acid sequence for human G3BP has GenBank Accession No. NP 005558 and UniProtKB/Swiss-Prot Accession No. Q08380 (SEQ ID NO: 1) and the amino acid sequence for dog G3BP has GenBank Accession No. XP 540464.2 (SEQ ID NO: 2). However, it is expected that G3BP from other species, including but not limited to human, also interacts with AAV. G3BP from other species include Pongo abelii (UniProtKB/Swiss-Prot Accession No. Q5RDA4, homology 99%); Callithrix jacchus (UniProtKB/Swiss-Prot Accession No. A6MKVO, homology 92%); Canis lupus (GenBank Accession No. XP 540464.2, homology 72%); Bos Taurus (UniProtKB/Swiss-Prot Accession No. A7E3W2, homology 68%) Thus, G3BP from these and other species are also contemplated for use the present invention. It is discovered that murine G3BP, however, does not interact with AAV. Murine G3BP has GenBank Accession No. Q07797 and homology of 68% with human G3BP.

In a preferred embodiment, G3BP is isolated or recombinant human G3BP. Commercial sources of recombinant and isolated human G3BP include: recombinant non-glycosylated G3BP (GenWay Biotech, San Diego, Calif.); recombinant non-glycosylated G3BP (ProSci INCORPORATED, Poway, Calif.); recombinant GST-tagged non-glycosylated G3BP (ABNOVA, Jhongli City Taiwan); recombinant glycosylated G3BP (proteolytically cleaved into two fragments) (R&D Systems, Minneapolis, Minn.).

Glycosylated G3BP can be prepared by methods known to those skilled in the art. For instance, glycosylated proteins can be produced in mammalian or insect cells, preferably in human cells, by using cell culture or bioreactors. Glycosylated proteins can then be purified using various chromatography methods. Glycosylated proteins can also be produced in transgenic animals and purified as described above.

The present invention also contemplates the use of isolated variants of G3BP. Such isolated G3BP variants can be generated by any suitable technique known in the art. For example, one or more amino acid residues of the G3BP amino acid sequence may be deleted or substituted with any of the known naturally-occurring or synthetic amino acids or analogs. Further, additional amino acid residues may be inserted into the G3BP amino acid sequence. G3BP variant constructs and wild-type G3BP constructs can be expressed using any suitable expression system, for example, using a baculovirus-insect cell expression system, which is particularly useful for expressing glycoproteins.

G3BP variants are expected to work as long as they maintain the ability to interact with AAV and/or other viruses disclosed herein (e.g., adenovirus, herpes virus, varicella virus, influenza virus, and the like). The sequence identity between human and dog G3BP, both of which interact with AAV, is 72%. The sequence identity between human and murine G3BP, murine G3BP not having the ability to interact with AAV, is 68%. The sequence identity between human and pongo abelii G3BP is 99%. The sequence identity between human and callithrix jacchus G3BP is 92%. The sequence identity between human and bos taurus G3BP is 68%. Thus, G3BP from other species are also contemplated for use in the present invention. Preferably, the G3BP variant used in the present invention has a sequence identity with human G3BP of at least 72%, preferably of at least 80%, at least 85%, at least 90%, and most preferably at least 95%. The G3BP variant used is a functional variant, which means in the present invention that said G3BP variant retains the ability of human and dog G3BP to interact with, and lessen transduction efficiency of, viruses, in particular AAVs, most particularly AAV-1, -5, -6 and/or -8.

The G3BP proteins may be isolated by any suitable method known in the art, and further modified, if desired. For example, in certain embodiments of the invention, conjugates of G3BP are provided. In conjunction with the discovery that G3BP interacts with AAV and other viruses, conjugates of G3BP can be used to target and eliminate a virus in the bloodstream. For example, G3BP can be conjugated to an anti-viral agent or compound, which reduces or inhibits infectivity of the virus, thereby reducing tissue distribution of the virus. Methods for making protein conjugates are well known in the art and may be carried out according to any suitable method.

The present invention also contemplates the use of G3BP mimetic agents, such as members of the SRCR superfamily, which includes SCAVR, SPERR, CD5, and CD6 (see, Hohenester et al., 1999; Rodamilans et al. (2007), J Biol Chem; 7:12669-12677.

Methods of Treatment

In a specific embodiment, the present invention provides a method for increasing the efficiency of tissue penetration of AAV, in particular of AAV-1, -5, -6 and/or -8, most particularly AAV-6, in a patient in need thereof, which method comprises abrogating G3BP-mediated reduction of AAV tissue penetration.

In some embodiments of the invention, G3BP-mediated reduction of AAV tissue penetration can be abrogated by depleting G3BP from serum. G3BP can be depleted from serum by any suitable method, such as, but not limited to, depletion using bioaffinity chromatography (Haemonetics, Braintree, Mass.), immuno-affinity columns, or Galectin-3 or Galectin-1 columns. G3BP can also be depleted from serum by plasmapheresis. Effective depletion of G3BP can be determined by ELISA or any other method suitable for quantifying protein levels in a sample.

In another embodiment of the invention, an AAV-conjugated depletion column that can bind to and deplete G3BP and auxiliary proteins is contemplated.

In certain embodiments, G3BP can be depleted from serum by administering to a patient one or more of the depleting anti-G3BP antibodies, described above. Effective depletion of G3BP may be determined, e.g., by analyzing a serum sample from the patient and quantifying the amount of G3BP in the sample, by any method suitable for quantifying protein levels (e.g., ELISA, Western blot, etc.).

In certain other embodiments of the invention, abrogating G3BP-mediated reduction of AAV tissue penetration can be achieved using G3BP inhibitors or competitors, and/or neutralizing or depleting antibodies, described, supra (e.g., inhibitors/competitors such as, but not limited to, Galectin-1, Galectin-3, empty capsids, agnostic VPs, and the like, and anti-G3BP neutralizing or depleting antibodies, such as SP-2. In another embodiment, the invention relates to a method for increasing virus-mediated gene delivery in a subject, which method comprises neutralizing or depleting G3BP in said subject prior to or during said gene delivery. This method is particularly adapted to gene delivery mediated by AAV-1, -5, -6 and/or -8. Neutralization is achieved by using a G3BP inhibitor or a G3BP neutralizing compound as defined above. Other viruses include those viruses that compete with AAV-1, -5, -6 and/or -8 for a binding to G3BP.

In another specific embodiment, the present invention provides a method for reducing tissue distribution of a virus in a patient infected with a pathogenic virus or thought to be at risk for becoming infected with a pathogenic virus (e.g., a patient expressing low levels of G3BP or an organ transplant recipient), which method comprises administering to a patient in need thereof a composition comprising G3BP in an effective amount for reducing tissue distribution of the pathogenic virus (e.g., by retaining the virus in the serum).

While not intending to be bound by any particular theory or mechanism, it is believed that G3BP binds to the virus, causing aggregates of the virus to form [see, e.g., FIGS. 4 and 9]. The large viral aggregates are unable to pass from the bloodstream to the tissues, and are cleared by filtration organs such as the liver or phagocytosed by macrophages.

The methods and compositions of the instant invention are believed to be useful for reducing tissue distribution of viruses such as, but not limited to, influenza virus, hepatitis C virus (HCV), hepatitis B virus (HBV), adenovirus, various herpes simplex virus strains, varicella zoster virus, cytomegalovirus, Epstein-Bar virus (EBV), measles virus, rubeola virus, respiratory syncytial virus, rotavirus, metapneumovirus, norovirus, sapovirus, mumps virus, coxsackie virus, parvovirus, lyssavirus, and human immunodeficiency virus (HIV). The method is considered to work against HIV given the increase in G3BP levels in patients infected with HIV.

In a specific embodiment, the patient in need of reducing tissue distribution of a virus is an organ transplant patient. Thus, the present invention also contemplates administering a G3BP-containing composition of the invention directly to an organ recipient just prior to organ transplantation, simultaneously with organ transplantation, and/or soon after organ transplantation. The timing of such treatment can be readily determined by the patient's physician.

In still another embodiment, the present invention provides a method for reducing the amount of infective virus harbored by an organ destined for transplantation into a patient, which method comprises exposing said organ to G3BP in vitro in an effective amount for reducing the ability of the virus to spread to the patient's organs or tissues after transplantation.

It is desirable to treat organ transplant recipients or the organ destined to be transplanted with a G3BP-containing composition of the invention, because organs to be transplanted can harbor latent viruses that can infect the transplant recipient. This poses a significant threat to the transplant recipient, who typically will be treated with immunosuppressive drugs in order to prevent immunological rejection of the transplanted organ. When treated with such drugs, the immunosuppressed transplant recipient is unable to mount a protective immune response to the virus, and can quickly succumb to systemic viral infection, in which the virus spreads to organ tissues, and which can be lethal or life threatening. Thus, in conjunction with the present discovery that G3BP interacts with AAV and can reduce its tissue distribution, G3BP can be administered to a transplant recipient in order to treat viral infection. In other embodiments, an organ or other tissue may be treated in vitro with G3BP prior to transplantation.

For in vitro treatment of an organ prior the transplant, the organ is treated with G3BP in vitro. Following incubation with G3BP, the organ is washed and then transplanted to the patient. Such methods can include, but are not limited to, hypothermic perfusion, normothermic perfusion, or bathing the organ in a solution comprising an appropriate concentration of G3BP [see, Monbaliu and Brassil. (2010), Curr Opin Organ Transplant; February 1. Epub ahead of print].

Non-limiting examples of viruses that can be harbored by transplanted organs and which can cause systemic viral infections that are believed to be treatable using the compositions of the present invention include cytomegalovirus, various herpes simplex virus strains, influenza virus, hepatitis A virus, hepatitis B virus (HBV), hepatitis C virus (HCV), adenovirus, varicella zoster virus, Epstein-Bar virus, measles virus, rubeola virus, respiratory syncytial virus, rotavirus, metapneumovirus, norovirus, sapovirus, mumps virus, coxsackie virus, parvovirus, lyssavirus, and human immunodeficiency virus.

In another embodiment, a G3BP-containing composition of the invention is useful for delaying a systemic viral infection. The delay can be useful e.g., for giving a patient's immune system time to mount an effective response against the virus, before systemic infection occurs.

In yet another embodiment, G3BP interaction with AAV may be prevented by structurally modifying the AAV vector for administration to a patient, such that G3BP in the patient's serum no longer interacts with and/or prevents tissue distribution of AAV. In one non-limiting example, since AAV2, AAV7, AAV9 and AAV10 does not interact with human G3BP (FIG. 3), modifying the AAV vector such that it contains the AAV2, AAV7, AAV9 or AAV10 capsid would abolish the G3BP interaction.

In another specific embodiment, the invention provides a method of gene therapy of a subject, comprising administering to said subject an effective amount of a recombinant AAV6 vector comprising a therapeutic exogenous polynucleotide or oligonucleotide, wherein said vector comprises a mutated AAV6 VP protein that presents a decreased binding to G3BP in comparison to the non mutated form of the VP protein. In a particular embodiment, said mutation is K531E.

In another specific embodiment, the invention provides a method for increasing AAV6 virus-mediated delivery of a therapeutic exogenous polynucleotide or oligonucleotide in a tissue targeted by AAV6, comprising administering to a subject in need thereof an effective amount of a recombinant AAV6 vector comprising a therapeutic gene, wherein said vector comprises a mutated AAV6 VP protein that present a decreased binding to G3BP in comparison to the non mutated form of the VP protein. AAV6 has been shown to be able to target various tissues including, for example, muscle, cochlea (Kilpratick et al., 2011), dendritic cells (Ussher et al., 2010), osteoblasts (Jiang et al., 2010), lung (Halbert et al. 2010) and the retina (Klimczak et al., 2009).

Combination Therapies

In certain embodiments of the invention, combination therapies are also possible. For example, a composition containing G3BP can contain one or more additional agents which are useful for reducing tissue distribution of a virus. Such additional agents can also be administered as one or more separate compositions in addition to the G3BP-containing compositions of the invention. Such compositions may be administered at the same or different times, to the same or different sites, and by the same or different routes of administration. In certain embodiments, the additional agent can be an anti-viral agent, such as but not limited to Tamiflu (oseltamivir phosphate), acyclovir for herpes viruses, interferon/ribavarin for hepatitis viruses, anti-retroviral therapy, and specific or non-specific immunoglobulin treatment adapted to the virus in question.

In another embodiment of the invention, multiple compositions comprising G3BP neutralizing and/or depleting agents of the invention can be administered. Such compositions may be administered at the same or different time, to the same or different site, and by the same or different route of administration. For example, in a specific embodiment of the invention, a composition comprising one or more G3BP inhibitors and/or competitors is administered and a composition comprising a G3BP depleting antibody is also administered. The agents contained in each of these compositions can also be co-administered as a single composition. In certain embodiments, such combination treatments can increase the efficacy of G3BP depletion from the serum.

Pharmaceutical Compositions and Administration

While it is possible to use a composition provided by the present invention for therapy as is, it may be preferable to administer it in a pharmaceutical formulation, e.g., in admixture with a suitable pharmaceutical excipient, diluent, or carrier selected with regard to the intended route of administration and standard pharmaceutical practice. Accordingly, in one aspect, the present invention provides a pharmaceutical composition or formulation comprising at least one composition of the invention, or a pharmaceutically acceptable derivative thereof, in association with a pharmaceutically acceptable excipient, diluent, and/or carrier. The excipient, diluent and/or carrier must be "acceptable" in the sense of being compatible with the other ingredients of the formulation and not deleterious to the recipient thereof.

The compositions of the invention can be formulated for administration in any convenient way for use in human or veterinary medicine.

Pharmaceutical Carrier

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin (1990, Mack Publishing Co., Easton, Pa. 18042).

Formulations

The compositions and formulations of the present invention may comprise pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, and the like, or into liposomes. Hylauronic acid may also be used [see, for example, Remington's Pharmaceutical Sciences, 18th Ed. (1990, Mack Publishing Co., Easton, Pa. 18042), pages 1435-1712]. With regard to oral administration, G3BP is present in colostrum and milk. Formulations employing such a carrier are particularly suitable for oral delivery to neonates.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants, preserving, wetting, emulsifying, and dispersing agents. The pharmaceutical compositions may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Administration and Dosage

The compositions (e.g., pharmaceutical or vaccine compositions) and formulations of the present invention can be administered topically, parenterally, orally, by inhalation, as a suppository, or by other methods known in the art. The term "parenteral" includes injection (e.g., intravenous, intraperitoneal, epidural, intrathecal, intramuscular, intraluminal, intratracheal, or subcutaneous). The preferred route of administration of G3BP-containing compositions, G3BP mimetic-containing compositions, and G3BP neutralizing, depleting, or inhibiting agent-containing compositions of the invention is intravenous injection.

The compositions and formulations of the present invention may be administered to an animal, preferably a mammal, and most preferably a human.

The dosage of the compositions or formulations of the present invention will vary widely, depending upon the nature of the disease, the patient's medical history, age, body weight, sex, sensitivity, the frequency of administration, the manner and route of administration, the clearance of the agent from the patient, dosage period, drugs used in combination, and the like. The initial dose may be larger, followed by smaller maintenance doses.

For any composition or formulation used in the methods of the invention, the therapeutically effective dose can be estimated initially from animal models. Dose-response curves derived from animal systems are then used to determine testing doses for the initial clinical studies in humans. In safety determinations for each composition, the dose and frequency of administration should meet or exceed those anticipated for use in the clinical studies.

Toxicity and therapeutic efficacy of the compositions and formulations of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$. Compositions that exhibit large therapeutic indices are preferred.

The data obtained from the animal studies can be used in formulating a range of doses for use in humans. The therapeutically effective doses of in humans lay preferably within a range of circulating concentrations that include the $ED_{50}$ with little or no toxicity. The dosage can vary within this range depending upon the dosage form employed and the route of administration utilized. Ideally, a single dose of each drug should be used daily.

Administration of the compositions or formulations of the invention may be once a day, twice a day, or more often, but frequency may be decreased during a maintenance phase of the disease or disorder, e.g., once every second or third day instead of every day or twice a day. The dose and administration frequency will depend on the clinical signs, which confirm maintenance of the remission phase, with the reduction or absence of at least one or more, preferably more than one, clinical signs of the acute phase known to the person skilled in the art. More generally, dose and frequency will depend in part on recession of pathological signs and clinical and subclinical symptoms of a disease, condition or disorder contemplated for treatment with the present compounds.

The appropriate dose and dosage times under certain conditions can be determined by the test based on the above-described indices, but may be refined and ultimately decided according to the judgment of the practitioner and each patient's circumstances (age, general condition, severity of symptoms, sex, etc.) according to standard clinical techniques.

Keeping the above description in mind, in vitro dosages of G3BP should be sufficient to achieve serum concentrations of G3BP in humans effective to inhibit viral tissue distribution. Such serum concentrations typically range from about 5 to 10 µg/ml. Such serum concentrations can be achieved, for example, through intravenous injections of appropriate amounts of a 10 mg/L of a G3BP composition, administered in an amount of around 10-100 mg/kg.

Keeping the above description in mind, typical in vitro dosages of a G3BP mimetic agent (e.g, members of the SRCR superfamily) range from about 5 to 10 µg/ml. Typical dosages of a G3BP mimetic agent for in vivo administration would depend on the relative activity of the mimetic and may be higher or lower.

Analogous effective ranges can be worked out for a G3BP inhibitor (e.g., Galectin-1 or Galectin-3) or anti-G3BP antibody.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

The amounts of an inhibitor to be administered in order to achieve a reduction in the level of native G3BP in the subject being treated will depend on various parameters readily assessable by physicians. As mentioned above, representative parameters include the initial concentration of G3BP in the serum of the subject, the particular inhibitor used and its concentration, and can also include the general condition of the subject, which condition can have an impact on the dose to be administered. The person skilled in the art can determine the most adapted amount of inhibitor, for example an antibody against G3BP, by administering it at a low dosage starting for example at 0.1 mg/kg and increasing stepwise to 1 and up to 10 mg/kg and thereafter testing the level of G3BP in the subject's serum. Increasing amounts of the inhibitor can then be assessed until an amount adapted for decreasing G3BP to the desired level is reached. Of course, care will be taken to ensure that the benefits/risks ratio is acceptable and that the administered amounts are not toxic or does not result in unacceptable side effects. Typically, if an anti-G3BP antibody is used as an inhibitory agent to reduce G3BP level, this reagent can be applied in concentrations similar or higher to the concentrations of G3BP in the subject's serum.

Combinations and Kits

The present invention contemplates combinations of a first composition containing an effective amount of an AAV vector comprising a therapeutic polynucleotide or oligonucleotide, said amount being effective to repair, replace, skip or silence a defective gene in said subject, and a second composition comprising a compound inhibiting the ability of G3BP to bind to said vector, in an amount effective to decrease or abrogate the ability of the subject's native G3BP to reduce or delay tissue penetration of said vector, said first and second compositions for simultaneous or sequential administration to a subject. The two compositions may be conveniently provided in a kit.

EXAMPLES

The present invention is described further below in working examples which are intended to further describe the invention without limiting the scope therein. Examples 9 to 11 are prophetic.

Materials and Methods

The following materials and methods were employed in the Examples described below.

rAAV Production

Pseudotyped AAV vectors were generated by packaging AAV2-based recombinant genomes into AAV-1, 2, 5, 6, 8, 9 and 10 capsids using previously described methods. Adenovirus-free vectors were generated either by using a three-plasmid transfection of HEK293 cells (AAV-1, 2, 5, 6 and 9) (Penaud-Budloo et al., 2008; Boye et al.) or by triple infection of Sf9 cells (AAV-6, 8, 9 and 10) (DiPrimio et al). AAV vectors were purified either by affinity chromatography using AVB Sepharose HP (IA-beads) (GE Healthcare Life Sciences, Piscataway, N.J.) (Pang et al.), or by standard procedure including two cycles of cesium chloride or iodixanol gradient centrifugation (Polyak et al., 2008). The number of viral genomes (vg) was estimated by quantitative polymerase chain reaction (qPCR) of extracted vector DNA. The vector physical particles (pp) numbers were estimated either by an ELISA-based method or by quantification of VP3 protein after SDS-PAGE analysis stained with Coomassie G250 with Bovine Serum Albumin (BSA) as a standard.

Animals

Healthy C57BL/6 mice (4 weeks old) were used in the study. All the procedures involving animals were performed according to the guidelines of the Animal Ethical Committee of our Institute. All experiments were performed at least in duplicate and some in triplicate. For systemic delivery, 6×10E11 vg of rAAV-6 or 1×1OE1 1 vg of rAAV-9 coding for the murine secreted embryonic alkaline phosphatase MuSEAP (Denti et al., 2006) under the CMV promoter were injected into the lateral tail vein. For intramuscular delivery, 5×10E9 vg of rAAV-6 or 1 10E9 vg of rAAV-9 coding for MuSEAP were injected into the left tibialis anterior (TA) muscle after anesthesia by intraperitoneal injection of ketamine (ketamine) (100 mg/kg, sold under the trademark VIRBAC™) and xylazine (xylazine) (10 mg/kg, sold under the trademark ROMPUN™). Vectors and G3BP were incubated for 1 hr at ambient temperature before injections. The final volume was adjusted to 120 µl or 20 µl with phosphate buffer saline (PBS) for intravenous and intramuscular injections, respectively. Mice were sacrificed 2 weeks after injection and serum levels of MuSEAP were evaluated by chemo-luminescence reporter assay (sold by TROPIX, Bedford Mass.).

Sera

Commercially available human serum (SIGMA, St. Louis, Mo.) or serum samples obtained in accordance with regulatory guidelines from healthy human adults were used in the experiments. Canine sera were obtained from healthy dogs of 6 to 9 months of age (Ecole Nationale Vétérinaire d'Alfort). Macaque sera were obtained from the Ecole Nationale Vétérinaire de Nantes). Sera used in this study were seronegative for respective AAV serotypes and further processed by ultracentrifugation at 75,000 rpm for 2 hours (Beckman 100 ultra-centrifuge; TLA 100.4 rotor) before use in co-precipitation assays.

Co-Precipitation Experiments

Serum proteins interacting with rAAV were co-precipitated from serum by ultracentrifugation at 30,000 rpm for 2 hours at room temperature (Beckman 100 ultra-centrifuge; TLA 100.4 rotor). Pellets were washed with 4.7 ml of PBS and re-precipitated under the same conditions. Resulting precipitates were resuspended in 200 µl of PBS and proteins were precipitated with 2 volumes of cold acetone. For 2D gel electrophoresis, proteins were dissolved in 180 µL of rehydration buffer (7 M urea, 2 M thiourea, 1% v/v Triton X-100, 1% w/v ASB, 2% w/v CHAPS, and 20 mM DTT).

Co-Immunoprecipitation

Co-immunoprecipitation of serum proteins was performed with rAAV vectors immobilized on AAV capsid-specific immunoaffinity beads (AVB-Sepharose beads) (GE Healthcare Life Sciences, Piscataway, N.J.)) (Pang et al.). Immobilized rAAV vectors (5 µA of AVB Sepharose/1× 10E12 vector particles) were incubated with 400 µl of serum for 1 hour. Beads were collected by centrifugation and washed three times with 1×PBS. The immunoprecipitate was solubilised in the appropriate buffer for further analysis by 1D or 2D electrophoresis.

Serum Depletion of G3BP

Human serum was depleted of G3BP by incubation with anti-G3BP antibodies bound to magnetic beads during 2 hours at room temperature. Coupling of anti-G3BP antibodies (SP-2 mouse monoclonal IgG1 (MediaPharma, Italy)) to magnetic beads (Dynabeads M-450 Tosylactivated; Invitrogen, Oslo Norway) was performed according to the manufacturer's instructions. Five micrograms of antibody were used in a reaction with 25 IA of magnetic beads.

G3BP Purification from Human Serum

Human G3BP was purified with anti-G3BP antibodies bound to the magnetic beads. The beads were washed extensively with PBS supplemented with 0.5% of Triton X100, followed by PBS. The adsorbed proteins were eluted in 200 mM Tris buffer, pH 9.5. Typically 2.5 µg G3BP per 1 ml of serum was obtained.

Two-Dimensional Gel Electrophoresis (2-DE) and Protein Identification

2-DE gel analysis and identification of proteins separated by 2-DE were performed as previously described (Gregorevic et al, 2008). Tryptic monoisotopic peptide masses were searched by using Aldente software (version Nov. 2, 2008) (expasy.org/tools/aldente) in the UniProtKB/Swiss-Prot database (Release 56.9 of 3 Mar. 2009) or by Protein Prospector (prospector.ucsf.edu) in the NCBI (25 Nov. 2008) and UniProtKB (10 Jun. 2008) databases with the following parameters: human/mouse/dog species, one missed cleavage site and mass tolerance setting of 20 ppm. Partial chemical modification such as oxidation of methionine was taken into consideration for the queries. Highest confidence identifications have statistically significant search scores, are consistent with the gel region from which the protein was excised (MW and pi) and account for the extent of sequence coverage and the number of peptides matched.

Western Blot Analysis

Protein samples were separated by electrophoresis onto a 4-12% gradient SDS-polyacrylamide gel and transferred onto a PVDF-Plus membrane (Millipore). The following primary antibodies were used: goat polyclonal antibody to huG3BP (1:1000; R&D systems); goat polyclonal antibody to mouse CRP (1:1000; R&D systems), mouse monoclonal antibody to human CRP (1:250; R&D systems) followed by corresponding IRDye-800CW or IRDye-600CW conjugated antibodies (1:10,000) according to the manufacturer's instructions (LI-COR Bioscience). Infrared fluorescence of the secondary antibodies was read on the Odyssey Imaging System.

Transmission Electron Microscopy

Vector particles (1×10E11 physical particles) were applied to formvar coated copper grids then negatively stained with uranyl acetate (3%). Images were obtained with a JEOL JEM-100S Transmission electron microscope (magnification from 50,000 to 100,000).

Surface Plasmon Resonance Imagery (SPRi)

Experiments were performed using a SPRi machine from Genoptics. Vectors (0.2 µl of $10^{12}$ to $10^{13}$ pp/ml) were immobilized on a glass prism as described before (Nogues et al., 2010). A dose-dependent binding study was performed using several dilutions of G3BP (10 nM, 15 nm, 20 nM and 40 nM) with PBS as a running buffer. rAAV surface was regenerated by injection of 100 µl of 25 mM NaOH (Chenail et al, 2010). SPRi data were analyzed using BiaEvaluation software (Biacore).

Example 1 rAAV-6 Interacts with G3BP in Human and Dog Sera

We screened for proteins interacting with rAAV vectors in serum samples from different species. Proteins interacting with rAAV-6 were first assessed in AAV6-seronegative dog sera by using co-sedimentation assays and 2D gel analysis. In a reproducible manner, multiple spots with similar molecular weights (about 90 kD) and isoelectric points (5.0-5.2) were exclusively found in rAAV-6 driven precipitates (FIG. 1A, B). Mass spectrometry analysis identified these spots as galectin-3 binding protein (G3BP), a highly glycosylated glycoprotein enclosing a scavenger domain. We next aimed to confirm this finding in human serum. Here, proteins interacting with vectors were recovered via rAAV-6 immobilized on immuno-affinity AVB-Sepharose beads, which improved sensitivity and reduced non-specific hits. Consistent with previous experiments using dog sera, 2D gels of recovered material exhibited multiple spots with an apparent MW of 90 kD and pI of 5.1 (FIG. 1C, D). Again, these spots were identified as G3BP by MALDI-ToF analysis (12/35 peptide matching (33%); 21% of coverage; MOWSE score 1.58 10E6). Recognition of G3BP was further confirmed by Western blot analysis (FIG. 1E, F).

Legend of FIG. 1: Proteomic Analysis of Serum Protein Interactions with rAAV-6.

Dog serum proteins recovered by ultracentrifugation (40,000×g for 2 h) (A) in the absence or (B) presence of rAAV-6 (10E12 physical particles). Pellet proteins were analyzed using two-dimensional (2-D) polyacylamide gel electrophoresis (Coomassie staining) In the presence of rAAV-6, in addition to the AAV capsid proteins, VP1, VP2 and VP3, a number of protein spots were reproducibly detected (5 experiments), but not in the absence of rAAV-6. MALDI-ToF analysis identified these proteins as galectin 3 binding protein (G3BP). 2-D gel electrophoresis of human serum proteins recovered with AVB-Sepharose immuno-affinity beads, (C) beads alone, or (D) beads with rAAV-6. Proteins eluted from the adsorbed rAAV-6 particles included the G3BP protein, again identified by MALDI-ToF (5 experiments). Identification of G3BP was confirmed by Western blot analysis: (E) Coomassie staining of SDS-PAGE, (F) corresponding PVDF membrane probed with a goat polyclonal antibody against hu-G3BP (1:1000; R&D systems). Lanes 1 and 2: protein extracts from human serum recovered via AVB immuno-affinity beads with rAAV-6 or beads alone, respectively. Lane 3: 100 ng of recombinant non-glycosylated G3BP (65 kD MW). The AAV capsid proteins, VP1, VP2 and VP3, as well as serum G3BP (around 90 kD MW) were found in lane 1. Two faint bands of about 70 kD and 26 kD corresponding to N-terminal and C-terminal fragments were generated by proteolytic cleavage of G3BP (Koths et al., 1993; Sasaki et al., 1998). In lane 2, empty beads did not retain G3BP although some proteins could be recovered depending on washing stringency.

Example 2

Human G3BP Hampers rAAV-6 Recovery by Immunoaffinity Beads

Figure 2:
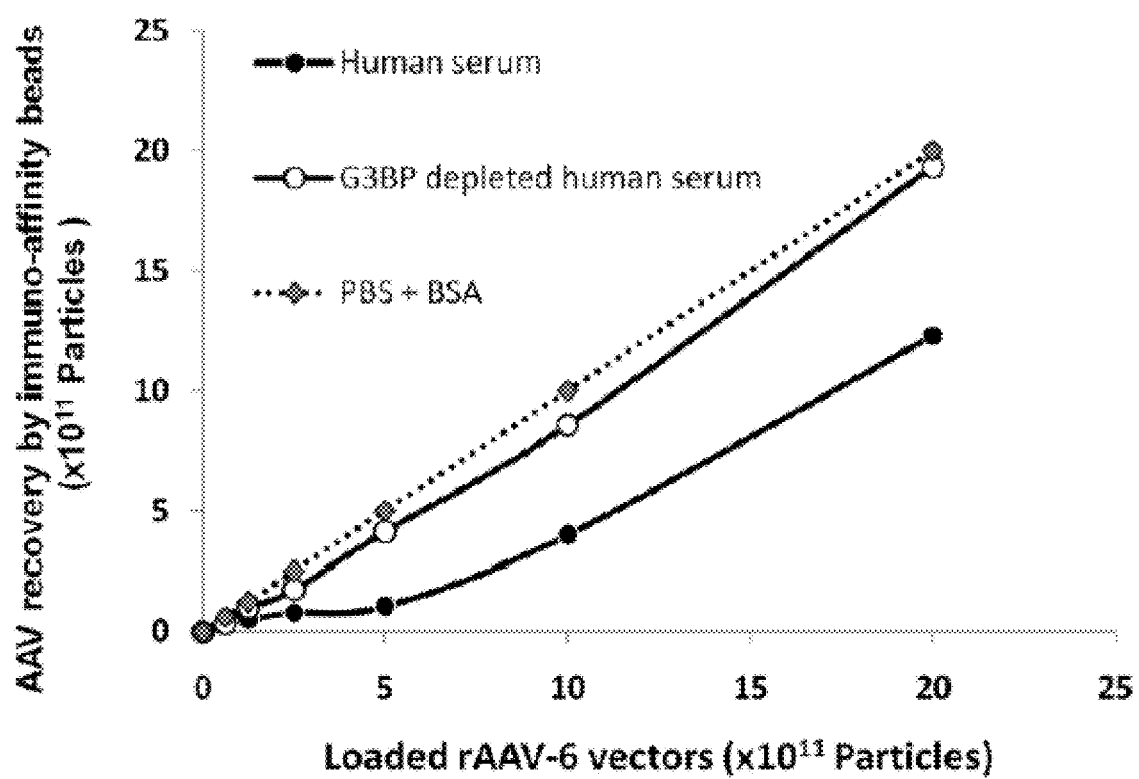
FIG. 2 is a graph depicting the effect of human G3BP on binding of rAAV-6 to AVB beads. Increasing amounts of rAAV-6 (from 10E11 to 2×10E12 physical particles) were incubated for 1 hour in the presence of PBS supplemented with 3% BSA (grey squares), AAV-6 seronegative human serum (filled circles), or the same serum immuno-depleted of G3BP by incubation with anti-G3BP antibodies bound to magnetic beads (open circles).

To determine whether hu-G3BP altered the binding of rAAV-6 to AVB-Sepharose beads, vectors were pre-incubated with either PBS supplemented with BSA, or human serum, or human serum depleted of G3BP by pre-incubation with immobilized anti-G3BP antibodies. Recovery of rAAV-6 in the PBS condition was linearly proportional to the concentration of physical vector particles (FIG. 2). In contrast, vector recovery in the presence of serum was compromised up to 8×10E11 physical particles (pp)/ml of vector, although it gradually increased and became parallel to the recuperation curve in PBS for high vector concentrations. Markedly, when serum was depleted of G3BP, rAAV-6 recovery was similar to the PBS condition, indicating that G3BP binding to rAAV-6 compromised either its affinity for AVB-Sepharose beads or altered its dispersion properties lowering the vector's access to beads.

Legend of FIG. 2. Human G3BP Hampers rAAV-6 Recovery by AVB beads.

Increasing amounts of rAAV-6 (from 10E11 to 2×10E12 physical particles) were incubated for 1 hour in the presence of either PBS supplemented with 3% of BSA (grey squares), or AAV-6 seronegative human serum (filled circles), or the same serum immuno-depleted of G3BP by incubation with anti-G3BP antibodies bound to magnetic beads (open circles). The amount of recovered rAAV-6 by AVB-Sepharose was estimated by quantification of the VP3 protein after fractionation by SDS-PAGE and Coomassie staining. In the presence of crude serum, vector recovery was partially compromised, thus confirming the presence of an interfering agent. Markedly, rAAV-6 recovery in the G3BP depleted serum was similar to the PBS condition, which displayed a linear relationship between load/recovery.

Example 3

Human G3BP Interacts Differentially with the Various rAAV Serotypes

Figure 3:
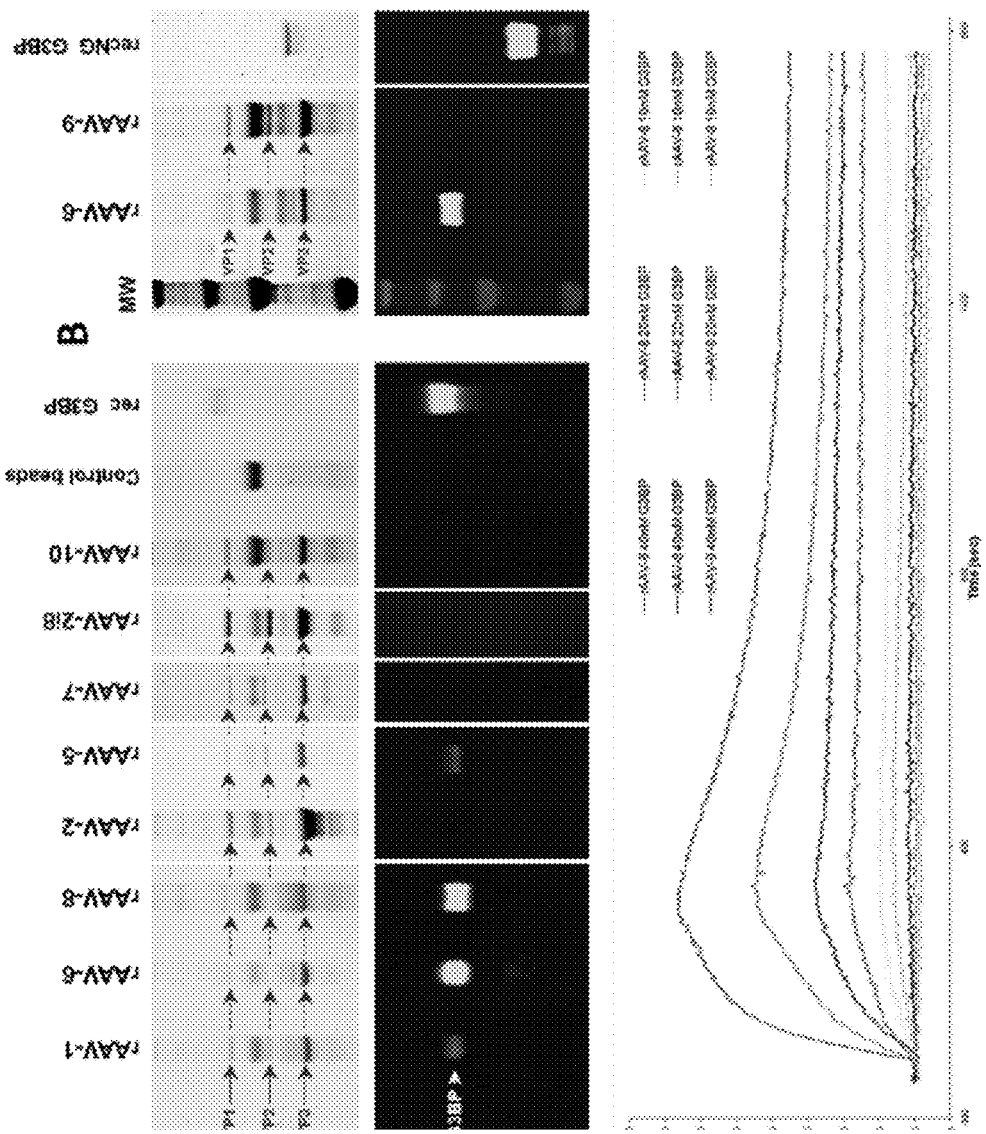
FIG. 3A is a Western blot showing the interactions between human G3BP and different rAAV serotypes immobilized on AVB-Sepharose beads.
FIG. 3B is a Western blot showing the interaction between rAAV-9 and human G3BP after ultracentrifugation. MW: molecular weight; rAAV serotypes are designated above the lanes; Control beads: AVB-Sepharose beads without rAAV; rec G3BP: recombinant glycosylated human protein; recNG G3BP: recombinant non-glycosylated human protein. Positions of G3BP and viral capsid proteins are indicated by arrows.
FIG. 3C is a graph depicting interactions of human G3BP with rAAV-6, -8, and -9 by surface plasmon resonance imagery.

In order to anticipate the most appropriate rAAV for clinical use under systemic delivery conditions, we investigated putative interactions of several serotypes (-1, -2, -2i8, -5, -6, -7, -8, -9 and -10) with G3BP in respective human seronegative sera. In these experiments, human sera were incubated with immobilized rAAVs, and Hu-G3BP recovery was appraised by Western blot analysis. In the case of rAAV-9, which does not bind AVB-sepharose beads, putative complexes were assessed by ultracentrifugation. Clearly, hu-G3BP was recovered in the presence of serotype-1, -5, -6 and -8, but not in presence of rAAV-2, -2i8, -7, -9 and -10 (FIG. 3 A). Binding affinities of rAAV-6, -8, -9 to hu-G3BP were further analyzed by using surface plasmon resonance imagery (SPRi) (FIG. 3 C). At all tested concentrations, rAAV-6 displayed the highest binding capacity to hu-G3BP while rAAV-9 did not show any binding. Interestingly, rAAV-8 exhibited about two times less binding capacity when compared to rAAV-6, although rAAV-6 and rAAV-8 $K_A$ values (association constants) for hu-G3BP were in the same order of magnitude (10E9 M$^{-1}$).

Legend of FIG. 3. Interaction of Hu-G3BP with Different Serotypes of rAAV.

Interactions of human G3BP with different rAAV serotypes were assessed by PAGE and Western blot analysis of serum proteins retained on rAAVs (serotypes-1, -6, -8, -2, -5, -7, -2i8, -10) immobilized on AVB-Sepharose beads (A). In the case of rAAV-9, interaction with hu-G3BP was assessed after ultracentrifugation (B). MW: molecular weights; rAAV serotypes are designated above the lanes; Control beads: AVB-Sepharose beads without rAAV; rec G3BP: recombinant glycosylated human protein; recNG G3BP: recombinant non-glycosylated human protein. Positions of G3BP and viral capsid proteins are indicated by arrows. (C) Interactions of hu-G3BP with rAAV-6, -8 and -9 were assessed by surface plasmon resonance imagery. rAAV vectors were immobilized on glass prisms and a dose-dependent binding study was performed using 10, 20 and 40 nM hu-G3BP.

Example 4

Human G3BP Aggregates rAAV-6

Figure 4:
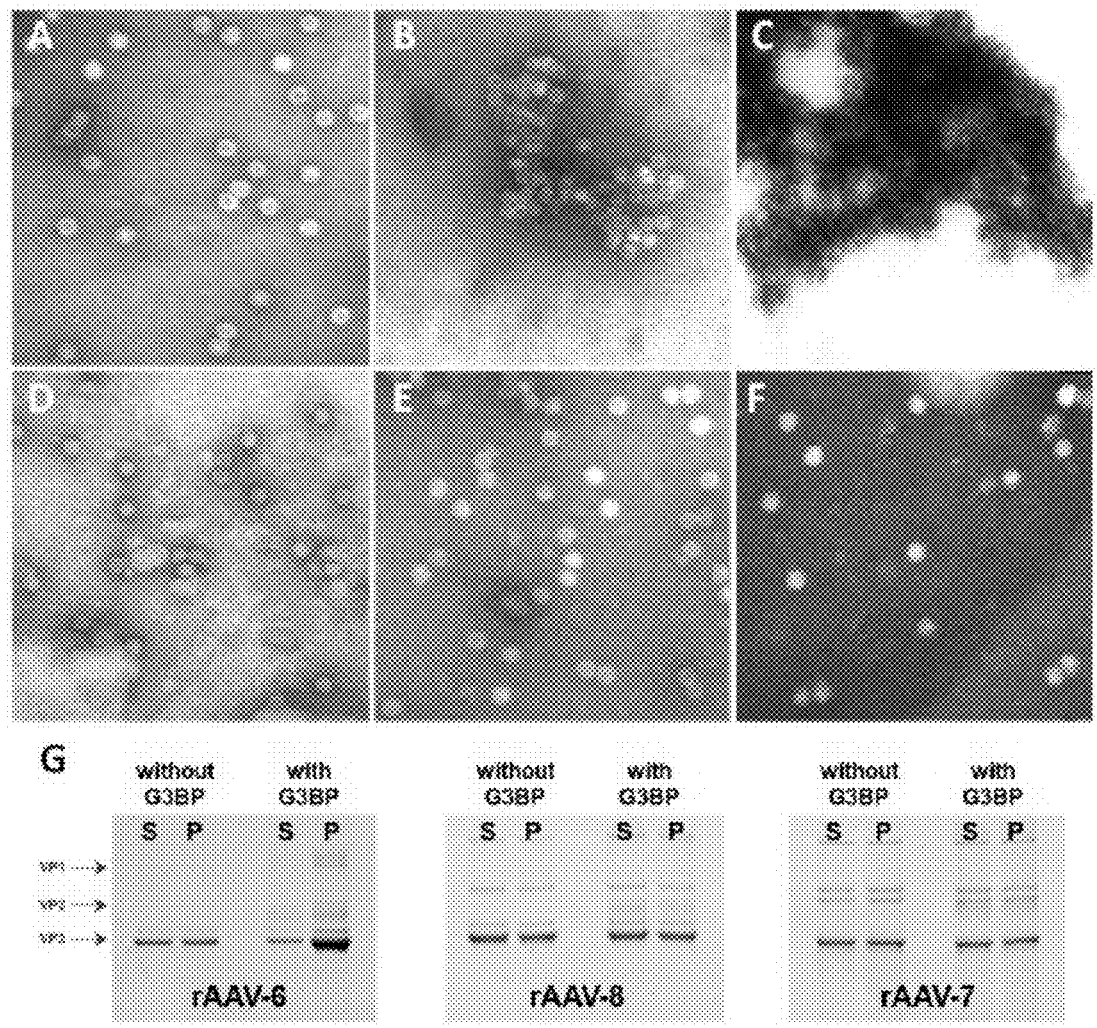
FIGS. 4A-F are electron micrographs depicting the formation of human G3BP/rAAV complexes as assessed by electron microscopy. rAAV6 was incubated in the presence of (A) 10 μg/ml of BSA, (B) BSA plus 1 μg/ml of hu-G3BP, or (C) BSA plus 10 μg/ml of hu-G3BP. Images were obtained using a transmission electron microscope (JEOL JEM-100S) at magnifications ranging from 50,000× to 100,000×, as indicated. rAAV9 was incubated in the presence of (D) 10 μg/ml of BSA, (E) BSA plus 1 μg/ml of hu-G3BP, or (F) BSA plus 10 μg/ml of hu-G3BP.
FIG. 4G is an image of a Coomassie stained gel showing aggregate formation with rAAV-6, -7, and -8 as assessed by low-speed centrifugation. Aggregates are preferentially found in the pellet (P) while free vectors are recovered in the supernatant (S). rAAV in the two compartments was estimated by Coomassie staining of viral proteins.

We first studied the interaction of hu-G3BP with rAAV-6 by electron microscopy (EM). rAAV-6 samples were diluted until vector particles appeared as unit-bodies scattered over the grid (FIG. 4 A). In the presence of 1 µg/ml hu-G3BP, some small vector aggregates were observed (FIG. 4 B). Increasing the hu-G3BP concentration up to 10 µg/ml induced the formation of large electron dense aggregates (FIG. 4 C). These aggregates were made of rAAV-6 and G3BP as shown by immuno-gold staining (FIG. 5). rAAV-9, in the same conditions of incubation, did not form any aggregate in the presence of hu-G3BP (FIG. 4 D, E, F). We also assessed the formation of aggregates by analyzing rAAV contents in supernatant and pellet after low speed centrifugation (FIG. 4 G). As expected from previous results, rAAV-6 but not rAAV-7 was found accumulated in the presence of G3BP in the pellet fraction. Intriguingly, rAAV-8 was not significantly precipitated by hu-G3BP despite the fact that binding assays clearly showed that both bound each other.

Legend of FIG. 4. rAAV-6 Aggregates with Hu-G3BP.

Formation of hu-G3BP/rAAVs complexes was assessed by electron microscopy. Aliquot of rAAV-6 (10E11 physical particles) were incubated in the presence of either: (A) 10 µg/ml of BSA, or (B) BSA plus 1 µg/ml of hu-G3BP, or (C) BSA plus 10 µg/ml of hu-G3BP. The mixtures were applied to a formvar coated copper grid and were negatively stained with uranyl acetate (3% solution). Images were obtained using a transmission electron microscope (JEOL JEM-100S) at magnification ranging from 50,000× to 100,000×, as indicated. Increasing the hu-G3BP concentration increased the formation of electron dense aggregates. (D, E, F) Electron microscopy analysis of rAAV-9 (10E11 vp) in the presence of either: (D) 10 µg/ml of BSA, (E) or BSA plus 1 µg/ml of G3BP, (F) or BSA plus 10 µg/ml of G3BP, respectively. Including huG3BP had no effect on the vector aggregation, thus indicating that complexation of huG3BP with rAAVs is serotype-dependent. (G) Putative aggregate formation with rAAV-6, -7 and -8 was assessed by low-speed centrifugation (10 minutes at 2000×g). In such conditions, aggregates are preferentially found in pellet (P) while free vectors are recovered in the supernatant (S). Reparation of rAAV in the two compartments was estimated by Coomasie staining of viral proteins.

Figure 5:
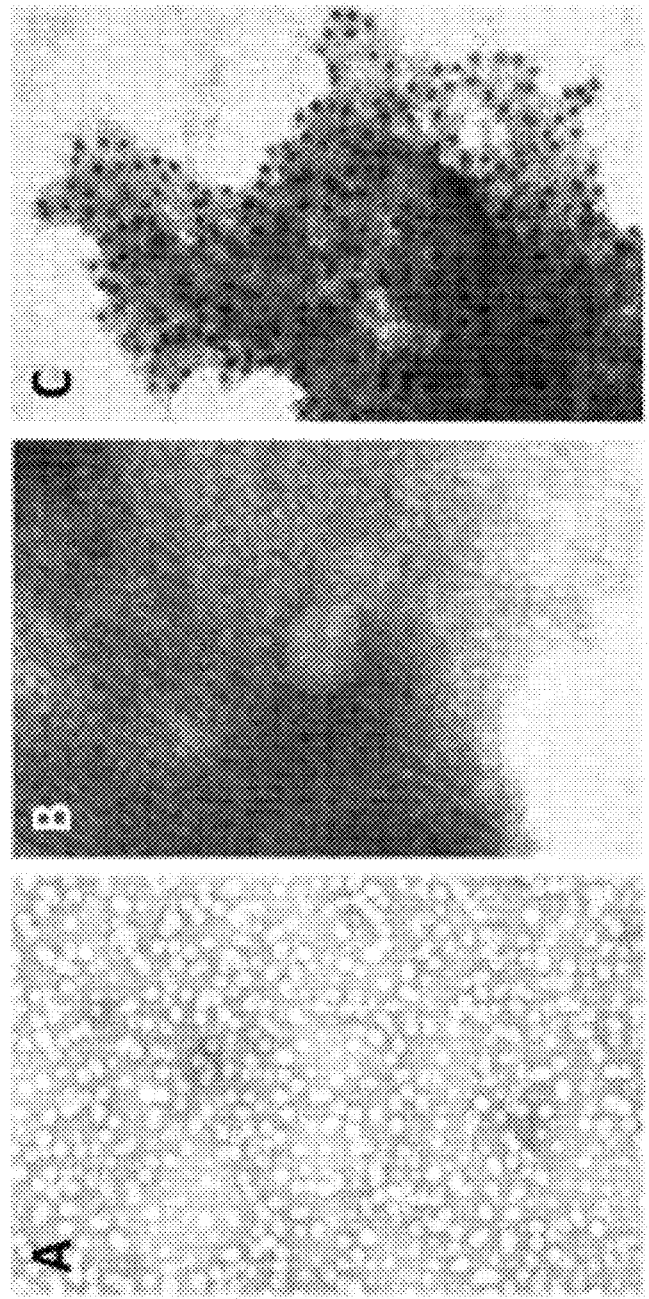
FIGS. 5A-C are transmission electron micrographs (magnification×50 000) of rAAV-6 alone (FIG. 5A), after incubation with human G3BP (FIG. 5B), and after staining complexes with an anti-human G3BP antibody and a secondary immune-gold antibody (Au 12 nm).

Legend of FIG. 5: rAAV-6 Forms Large Aggregates with Hu-G3BP.

Transmission electron microscopy (magnification×50 000) of (A) rAAV6 alone, (B) after incubation with hu-G3BP, and (C) after staining of complexes with an anti-hu-G3BP antibody revealed by a secondary immuno-gold antibody (Au 12 nm).

Example 5

Human G3BP Lessens Transduction Efficacy of rAAV-6 in Mouse

Figure 6:
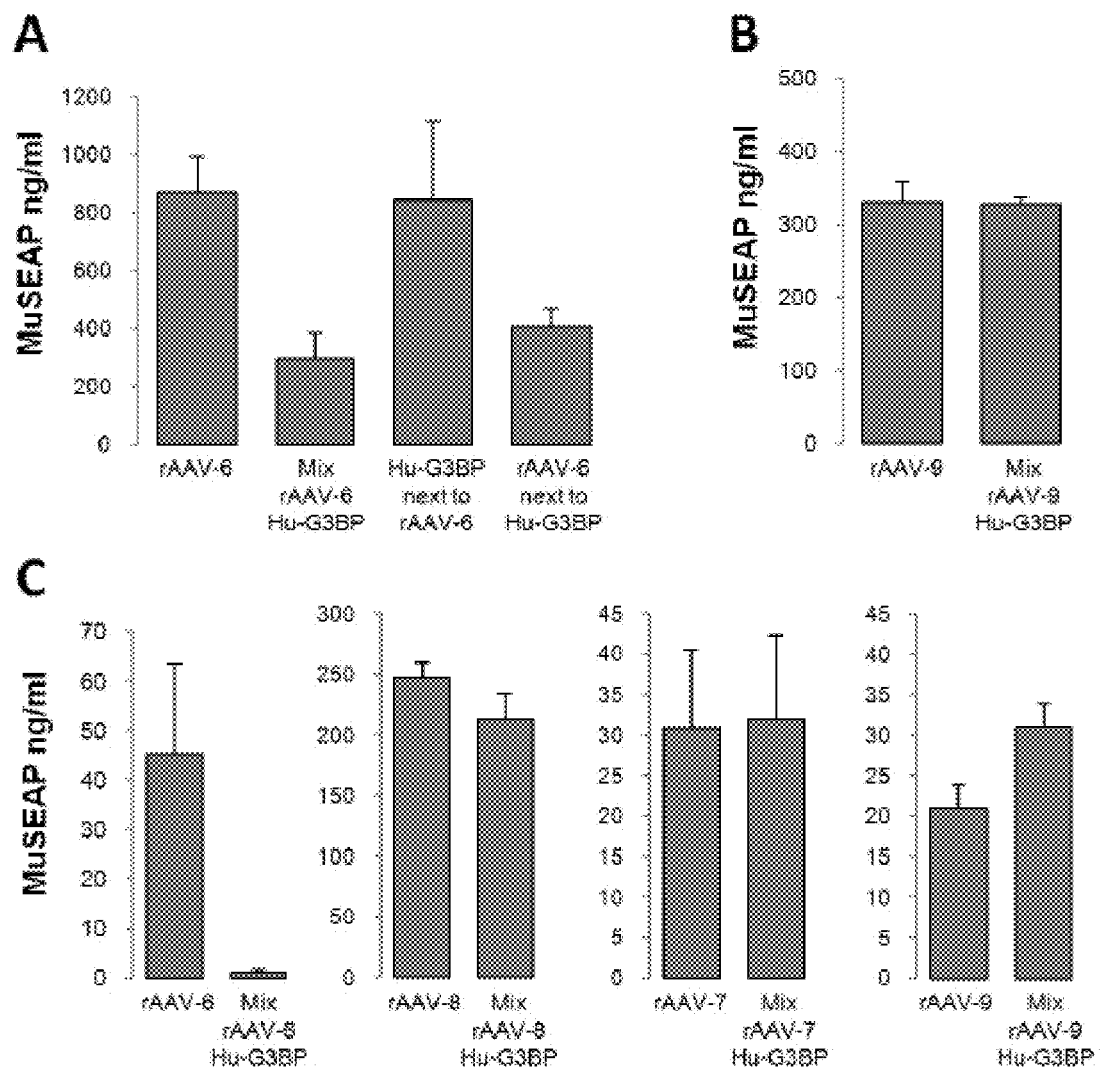
FIGS. 6A-D are graphs depicting serum levels of MuSEAP (ng/ml) in C57BL/6 mice two weeks after tail vein injection of rAAV-6 MuSEAP vectors. From left to right.

In order to study the impact of hu-G3BP on transduction efficiency in vivo, mice (C57BL/6) received intravenous injections of rAAV-6 encoding MuSEAP (murine secreted embryonic alkaline phosphatase as a gene reporter) alone or pre-incubated with purified hu-G3BP. Pre-incubation with hu-G3BP strongly inhibited transduction efficiency as demonstrated by the 3 times lower level of MuSEAP in serum two weeks after injection (296±87 ng/ml for rAAV-6/hu-G3BP vs 870±123 ng/ml for rAAV-6 alone) (FIG. 6 A). In a further experiment, hu-G3BP was intravenously injected one minute prior to rAAV-6. Markedly, hu-G3BP pre-conditioned mice displayed a significant decrease in MuSEAP levels (405±59 ng/ml) compared to mice injected with rAAV-6 only (870±123 ng/ml), thus demonstrating that blood-borne hu-G3BP hampered systemic spreading of rAAV-6. When the rAAV-6 (MuSEAP) was injected before hu-G3BP (one minute interval), subsequent serum levels of MuSEAP were not significantly different from controls (842±271 vs 870±123 ng/ml, respectively), suggesting that rAAV-6 had already reached its targets ahead of the subsequent hu-G3BP injection. In contrast, co-injecting hu-G3BP with rAAV-9 (MuSEAP) did not perturb transduction efficiency as shown by unchanged MuSEAP levels (FIG. 6 B), confirming that rAAV subtype-specific interactions with huG3BP constitute an innate defense mechanism. G3BP impact on transduction efficiency was also assessed by intramuscular injections. Pre-incubation of rAAV-6 with hu-G3BP completely abrogated transduction of muscle fibers, while the same procedure did not abridge rAAV-7 and rAAV-9 efficiencies (FIG. 6 C). As well, pre-incubation of rAAV-8 with hu-G3BP had no effect when delivered intramuscularly. This is consistent with results mentioned above showing that even though rAAV-8 could bind hu-G3BP, such interaction did not lead to the formation of large perceptible aggregates, which are likely responsible for most of the loss of transduction activity.

Legend of FIG. 6. Human G3BP Attenuated Differentially Transduction Efficacies of rAAVs Following Either Systemic or Intramuscular Delivery.

(A) Serum levels of MuSEAP (ng/ml) in C57BL/6 mice two weeks after tail vein injection of rAAV-6 MuSEAP vectors. From left to right: 6×10E11 rAAV-6 in PBS; 6×10E11 rAAV-6 pre-incubated with hu-G3BP (20 µg/ml); 6×10E11 rAAV-6 in PBS followed by an injection of 20 µg of hu-G3BP; injection of 20 µg of G3BP followed by an injection of 6×10E11 rAAV-6. (B) Serum levels of MuSEAP (ng/ml) two weeks after systemic injection of 10E11 rAAV-9 MuSEAP vectors in PBS (left) or mixed with 20 µg/ml hu-G3BP (right). (C) MuSEAP levels following single intramuscular injections of 5×10E9 rAAV-6 MuSEAP alone and in combination with 20 µg/ml hu-G3BP; similar experiments were carried out with 5×10E9 rAAV-8, 5×10E9 rAAV-7 and 10E9 rAAV-9 MuSEAP. At least three mice were used in each assay.

Example 6

G3BP interaction with AAV6 Prevents Vector Recovery in a Dose Dependent Manner

Figure 7:
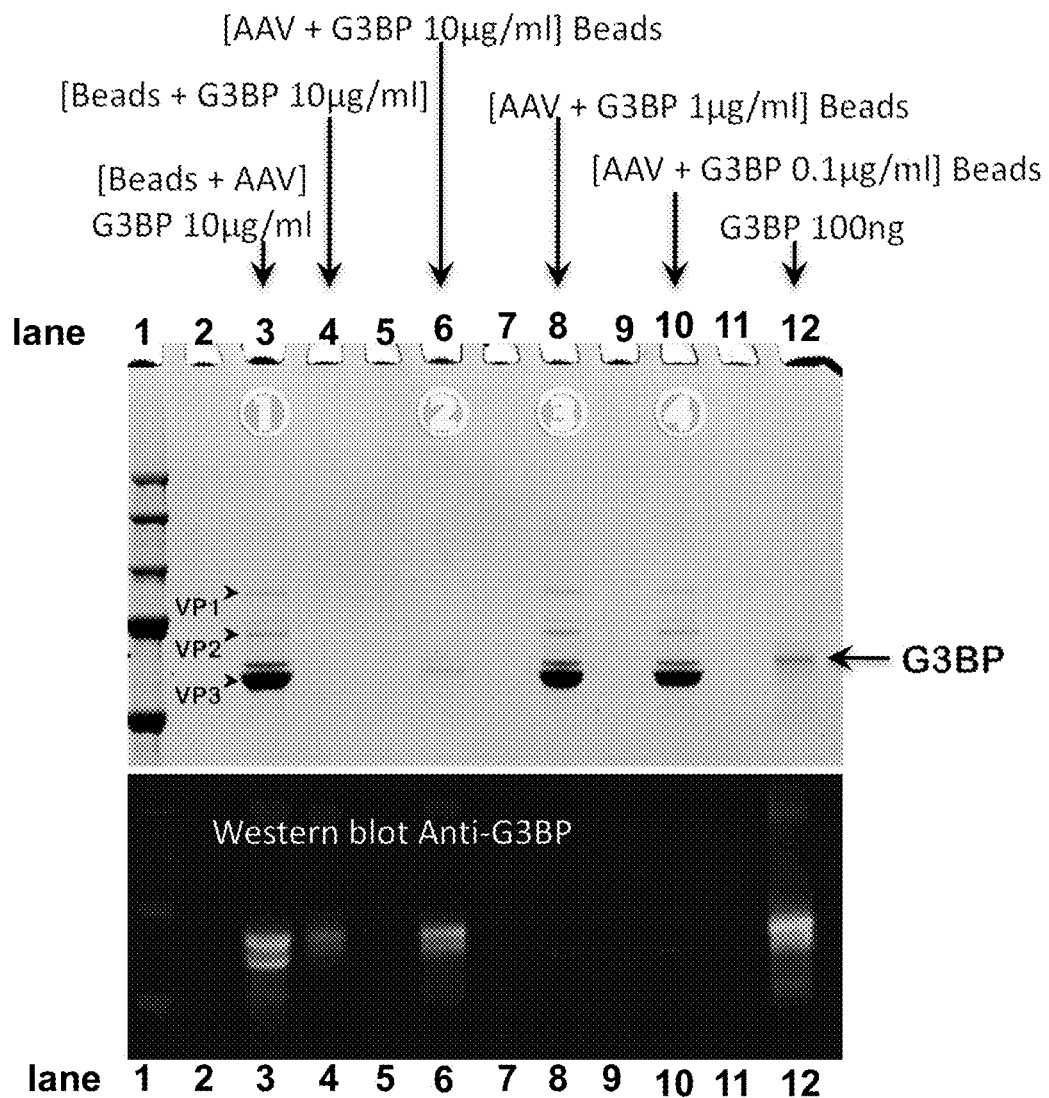
FIG. 7 is an image of a Coomassie-stained gel (upper panel) and a Western blot (lower panel) of the indicated groups. In the lower panel, the blot was stained with anti-human G3BP antibody. Lane 1: molecular weight marker; lane 3: "[Beads+AAV] G3BP 10 mg/ml" (Immunoaffinity (IA) beads ("Beads") preincubated with AAV, followed by incubation with G3BP); lane 4: "[Beads+G3BP 10 mg/ml]" (Beads incubated with G3BP but no AAV); lane 6: "[AAV+G3BP 10 mg/ml] Beads" (AAV preincubated with indicated amount of G3BP, followed by incubation with Beads); lane 8: "[AAV+G3BP 1 mg/ml] Beads" (AAV preincubated with indicated amount of G3BP, followed by incubation with Beads); lane 10: "[AAV+G3BP 0.1 mg/ml] Beads" (AAV preincubated with indicated amount of G3BP, followed by incubation with Beads); lane 12: recombinant G3BP alone (MW~62 kDa).

AAV6 was incubated with different concentrations of recombinant G3BP (GenWay Biotech, San Diego, Calif.) followed by incubation with IA-beads (5 µl of AVB Sepharose/1×10$^{12}$ vector particles) for 1 h. Samples were analyzed on 1D SDS-PAGE [Coomassie staining (upper panel) and Western blot (lower panel)] (FIG. 7).

In the first group (Group #1: [Beads+AAV] G3BP 10 µg/ml), as a control experiment, AAV6 was first incubated with IA-beads, then exposed to recombinant human non-glycosylated G3BP (10 µg/ml). As expected, based on the results of Example 3, supra, immobilized AAV6 retained G3BP, as indicated by the presence of a band at about 90 kDa (FIG. 7, upper panel, lane 3) and positive staining with anti-G3BP specific antibody in the Western analysis (FIG. 7, lower panel, lane 3).

In another group (Group #2), in order to test if G3BP could prevent interaction of AAV6 with the IA beads, AAV6 was first incubated in the presence of recombinant human non-glycosylated-G3BP (10 µg/ml), then recovery was tested on IA-beads (Group #2: [AAV+G3BP 10 µg/ml] Beads). In this condition, G3BP significantly prevented AAV6 recovery on the IA beads (FIG. 7, upper and lower panels, lane 6). Interestingly, the very few AAV particles that were retained by IA-beads bind relatively higher levels of G3BP compared to Group #1, as determined by Coomassie staining of VP3 for AAV particles, and Western blot for associated G3BP.

The ability of G3BP to inhibit AAV binding to IA beads (again by first incubating AAV6 in the presence of G3BP following by incubation of AAV6 with AAV-specific IA beads) at different concentrations (1 µg/ml and 0.1 µg/ml) was also tested (Groups #3 (lane 8) and #4 (lane 10), respectively). It was found that 1 µg/ml G3BP and below did not significantly affect AAV6 recovery by IA-beads, indicating that greater concentrations of G3BP are required to inhibit AAV6 binding to IA beads. Further, under these conditions, G3BP was not associated with recovered-AAV6. (FIG. 7, upper and lower panels, lanes 8 and 10). As a control, G3BP was incubated with Beads alone ([Beads+G3BP 10 µg/ml]) (lane 4). No bands were detected in the gel by Coomassie staining (FIG. 7, upper panel, lane 4). A feint band could be visualized by Western blot for G3BP, but this band correspond to non-specific G3BP binding to the beads and could be removed completely under more stringent washing conditions without influencing specific AAV-G3BP binding (FIG. 7, lower panel, lane 4), indicating that the presence of AAV is required for G3BP retention on the IA beads.

Figure 8:
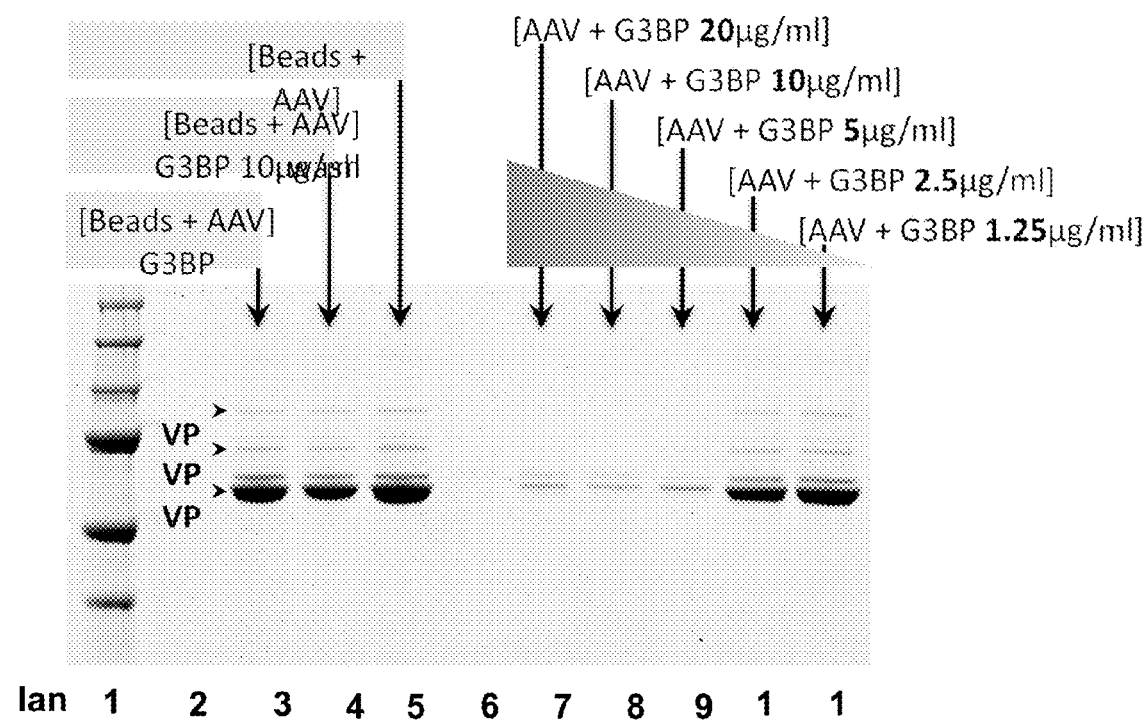
FIG. 8 is an image of a Coomassie-stained gel showing the effect of increasing concentrations of recombinant G3BP on the ability of AAV6 to bind AAV-specific IA beads ("Beads"). Lane 1: molecular weight marker; lane 3: "[Beads+AAV] G3BP 10 μg/ml" (Beads preincubated with AAV, followed by incubation with G3BP); lane 4: "[Beads+AAV] wash G3BP 10 μg/ml" (Beads preincubated with AAV, followed by wash and incubation with G3BP); lane 5: "[Beads+AAV]" (Beads incubated with AAV, no G3BP incubation); lanes 7-11, AAV preincubated with the indicated concentration of G3BP, followed by incubation with Beads.

Additional concentrations of G3BP, ranging from 20 µg/ml to 1.25 µg/ml, for preventing AAV binding to IA beads were also tested, the results of which are shown in FIG. 8. AAV6 recovery was similarly affected at G3BP concentrations higher than 5 µg/ml. At G3BP concentrations of 2.5 µg/ml and below, AAV6 recovery was not affected (FIG. 8).

Importantly, normal circulating levels of G3BP in human serum are about 5 µg/ml to about 10 µg/ml, concentrations shown in this Example to be sufficient to neutralize AAV. Thus, this indicates that AAV6 can be easily "neutralized" by G3BP when injected through the systemic pathway (e.g., into the bloodstream) in vivo. Thus, it is presently discovered that reducing circulating G3BP below 2.5 µg/ml can improve widespread delivery (tissue distribution) of AAV6 vectors in a subject.

Figure 9:
FIG. 9 is a schematic displaying interactions of G3BP (rods) with AAV (spheres) and IA beads coated with AAV-specific antibody (Y-shape) (See FIGS. 7 and 8 for experimental data). In (1): Interaction of G3BP with AAV immobilized on IA beads; (2) Incubation of AAV with an excess of G3BP followed by interaction with IA beads (high concentration of G3BP favors G3BP polymerization (Muller, Sasaki et al. 1999; Hellstern, Sasaki et al. 2002), and complexes of G3BP/AAV escape binding by IA beads); (3, 4) Incubation of AAV in the presence of low concentration of G3BP, followed by incubation with IA beads (at low concentrations, G3BP does not form polymers, does not interact with AAV, and does not prevent AAV binding to IA beads. This was shown for non-glycosylated G3BP (FIG. 8), but glycosylated G3BP interacts with AAV at all concentrations tested, data not shown).

FIG. 9 is a schematic explanation of interactions of G3BP (rods) with AAV (spheres) and IA beads coated with AAV-specific antibody (Y-shapes) (See FIG. 8 for experimental data). In (1): Interaction of G3BP with AAV immobilized on IA beads; (2) Incubation of AAV with an excess of G3BP followed by interaction with IA beads (high concentration of G3BP favors polymerization of G3BP (see, Muller, Sasaki et al. 1999; Hellstern, Sasaki et al. 2002) and complexes of G3BP/AAV escape binding by IA beads); (3, 4) Incubation of AAV in the presence of low concentration of G3BP followed by incubation with IA beads (at low concentrations, G3BP does not form polymers, does not interact with AAV, and does not prevent AAV binding to IA beads. While this was shown for non-glycosylated G3BP (FIG. 8), glycosylated G3BP interacts with AAV at all concentrations tested (data not shown).

Example 7

Interaction of G3BP with AAV6 is Abrogated in Human and Canine AAV6-Seropositive Serum It was next determined whether G3BP present in human serum from AAV6 seronegative (FIG. 10, upper panel) or seropositive (FIG. 10, lower panel) individuals interacted with AAV6 using 2D gel electrophoresis. Serum samples were preconditioned by ultracentrifugation (2 hours at 75,000 rpm, using a Beckman 100 ultra-centrifuge with a TLA 100.4 rotor, at room temperature), and then incubated for 1 hour at 4° C. in the presence of AAV6 (10$^{12}$ vg/ml). Samples were then centrifuged for 2 hours at 30,000 rpm at room temperature. Subsequent pellets were washed with 4.7 ml of 1×PBS and re-precipitated under the same conditions. Resulting precipitates were resuspended in 200 µl of 1×PBS and proteins were precipitated with 2 volumes of cold acetone. For 2D gel electrophoresis, protein extracts were dissolved in 180 µL of rehydration buffer (7 M urea, 2 M thiourea, 1% v/v Triton X-100, 1% w/v ASB, 2% w/v CHAPS, and 20 mM DTT). Protein contents were analyzed by 2D gel electrophoresis.

Figure 10:
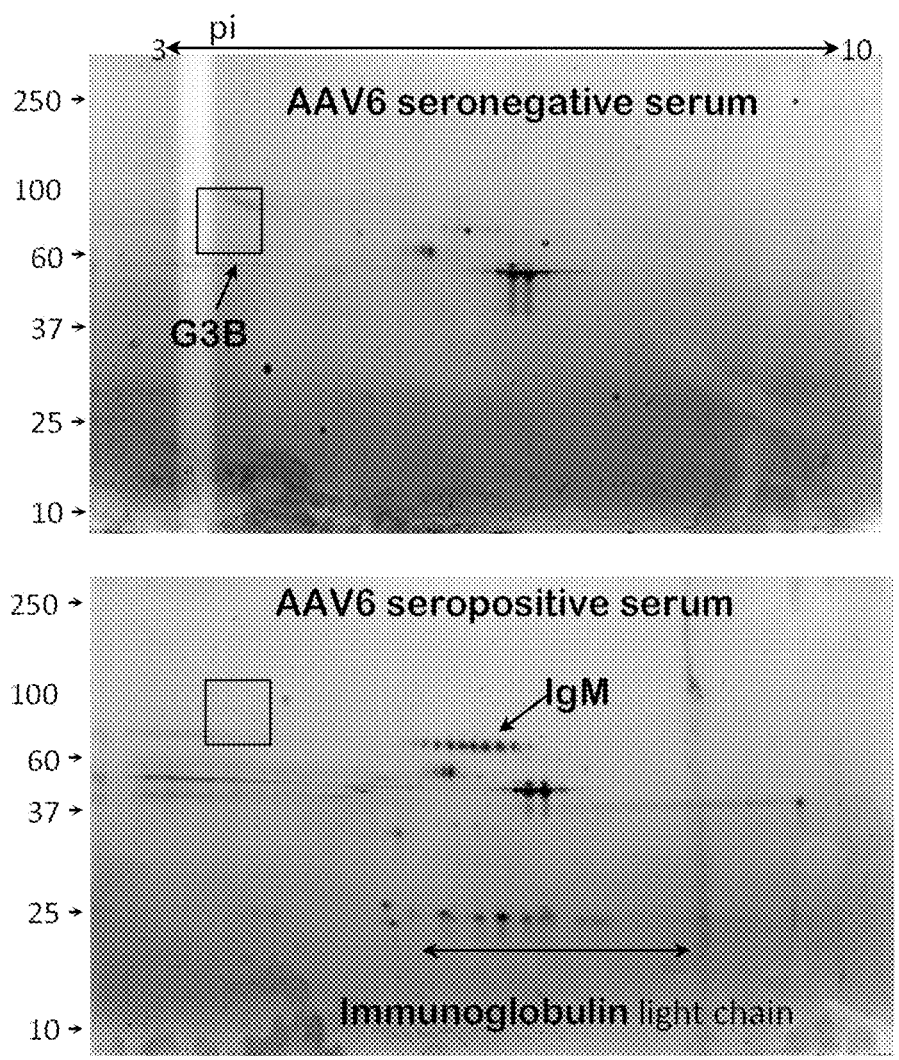
FIG. 10 shows images of two Coomassie-stained 2D gels for analysis of G3BP retention by AAV6 in AAV6 seronegative (upper panel) and seropositive (lower panel) human serum. The expected position of G3BP in the gel is boxed. In the lower panel, arrows are drawn to IgM and Immunoglobulin light chain.

In AAV-seronegative individuals, G3BP bound to AAV6 and was detected by subsequent 2D gel analysis (Comassie blue staining) (FIG. 10, upper panel), consistent with the results shown in Example 2, supra. In contrast, G3BP was not retained and hence was not detected by 2D gel analysis in serum from AAV seropositive individuals (FIG. 10, lower panel). VP1, VP2 and VP3, as well as different immunoglobulin chains were recovered in this group, however, indicating that AAV-specific antibodies bound to AAV and prevented the interaction between G3BP and AAV (FIG. 10, lower panel).

Figure 11:
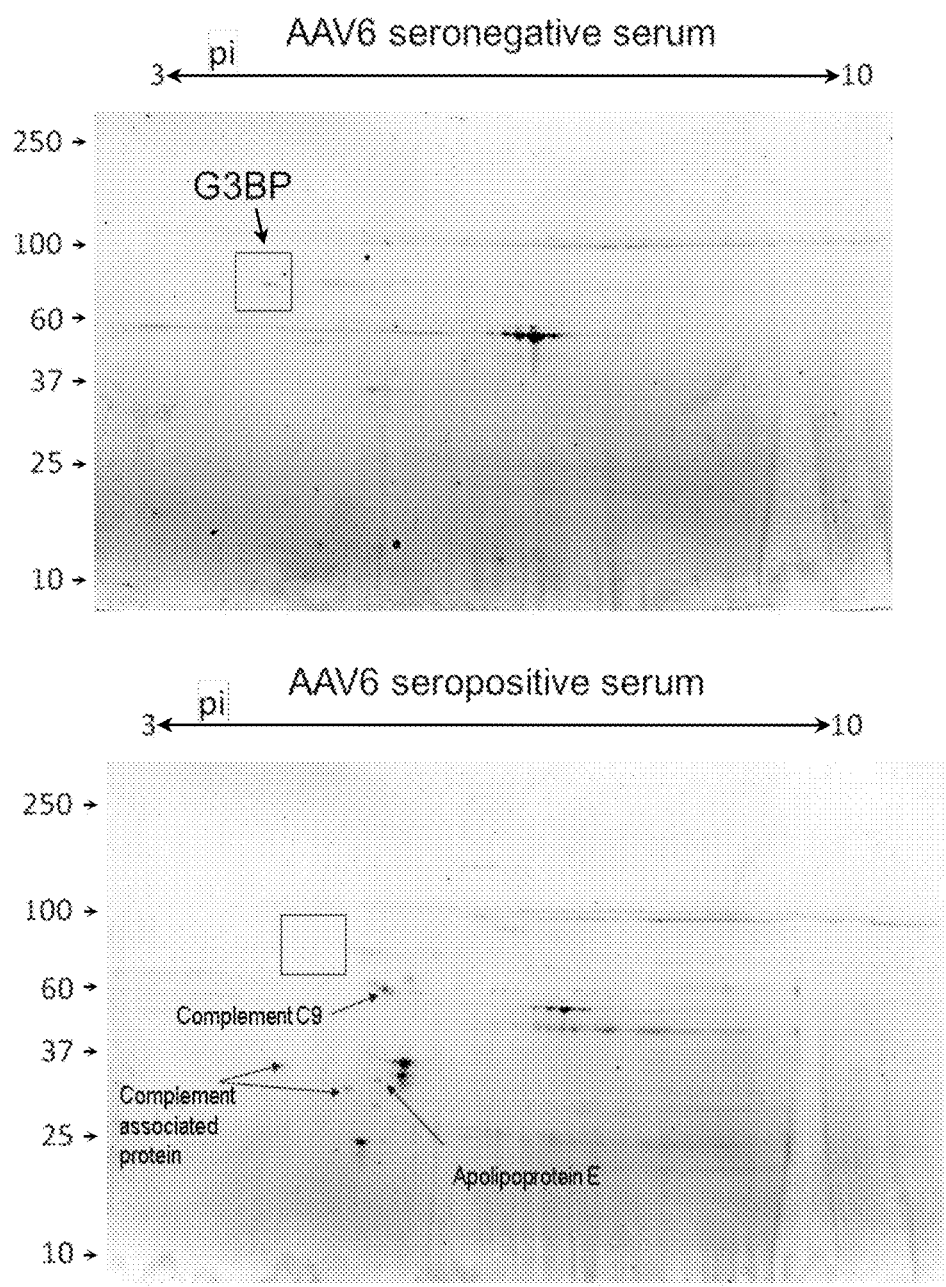
FIG. 11 shows images of two Coomassie-stained 2D gels for analysis of G3BP retention by AAV6 in AAV6 seronegative (upper panel) and seropositive (lower panel) dog serum. The expected position of G3BP in the gel is boxed. In the lower panel, arrows are drawn to Complement C9, Complement associated protein and Apolipoprotein E.

AAV seronegative and seropositive dog serum was also tested using the same protocol described for human serum, with similar results (FIG. 11). While AAV6 retained G3BP in AAV seronegative serum (FIG. 11, upper panel), G3BP could not be detected in AAV seropositive serum (FIG. 11, lower panel). In the AAV6 seropositive serum, VP1, VP2 and VP3, as well as different immunoglobulin chains and components of the complement system were identified (FIG. 11, lower panel).

Figure 12:
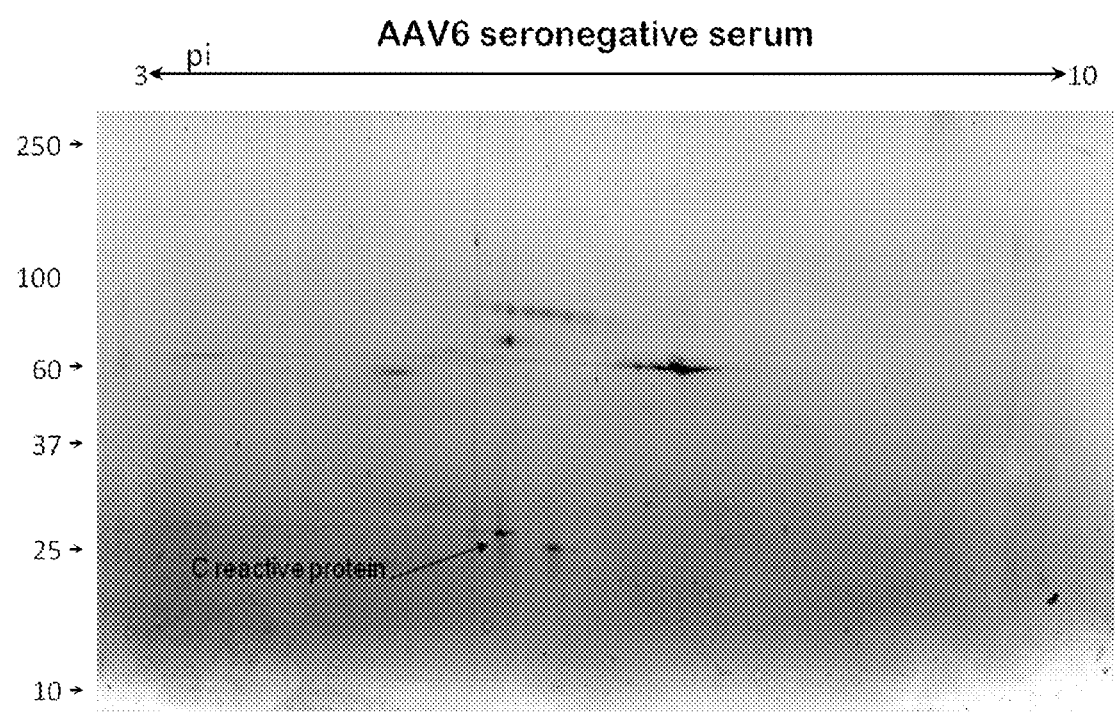
FIG. 12 is an image of a Coomassie-stained 2D gel for analysis of G3BP retention by AAV6 in AAV6 seronegative murine serum. The arrow is drawn to C reactive protein (CRP).
Figure 14:
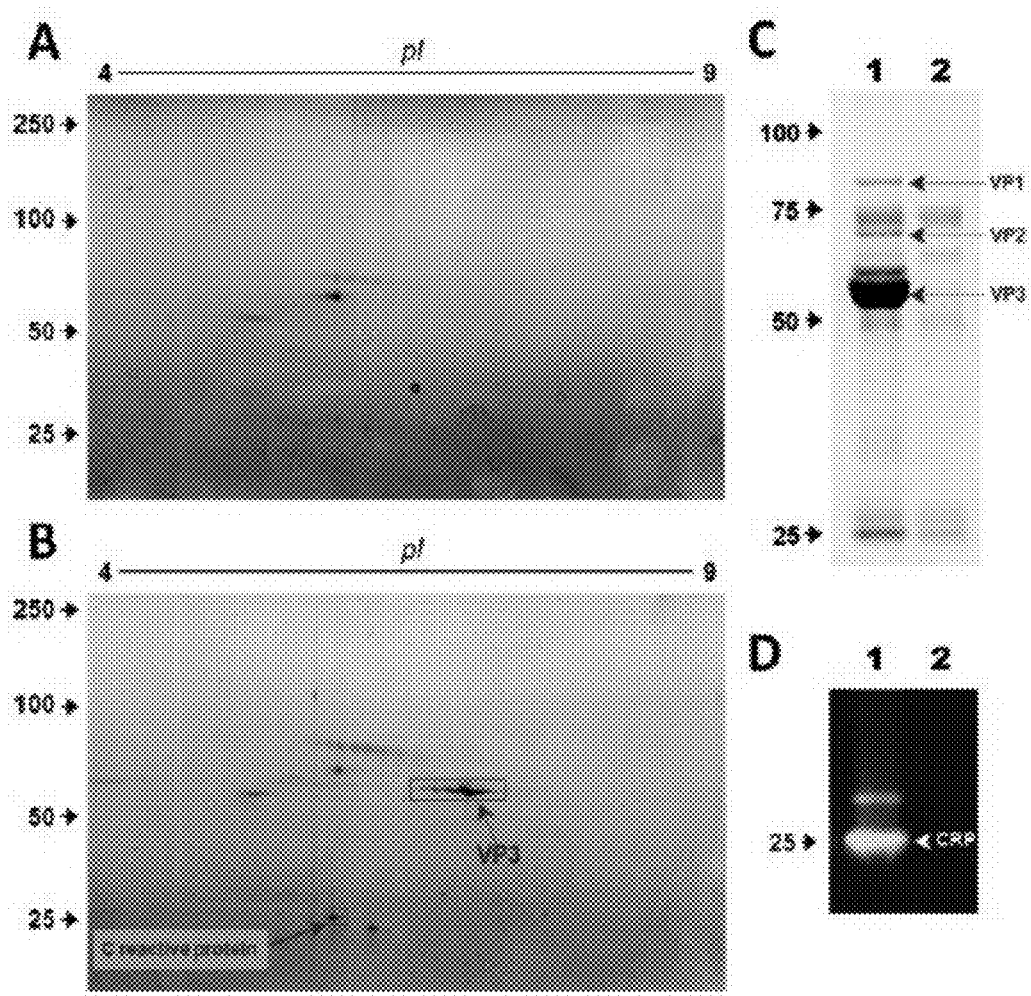
FIGS. 14A and B are images of Coomassie-stained 2D gels for analysis of mouse serum proteins bound to AVB-Sepharose alone (FIG. 14A) or rAAV-6 bound AVB-Sepharose beads (FIG. 14B). The arrow indicates the position of mouse C-reactive protein (CRP).
FIGS. 14C and D are images of a Coomassie stained gel (FIG. 14C) and corresponding Western blot (FIG. 14D) using a goat polyclonal antibody (primary) against mouse CRP (1:1,000; R&D systems) and a species anti-goat IRDye-800CW conjugated secondary antibody (1:10,000). Lanes 1 and 2: protein extracts from mouse serum recovered via AVB-Sepharose immuno-affinity beads, loaded with rAAV-6 or buffer alone, respectively. VP1, VP2 and VP3 as well as serum CRP (around 25 kD MW) were detected in lane 1. In lane 2, beads alone did not retain CRP although some other unidentified proteins were recovered depending on washing stringency.
Figure 15:
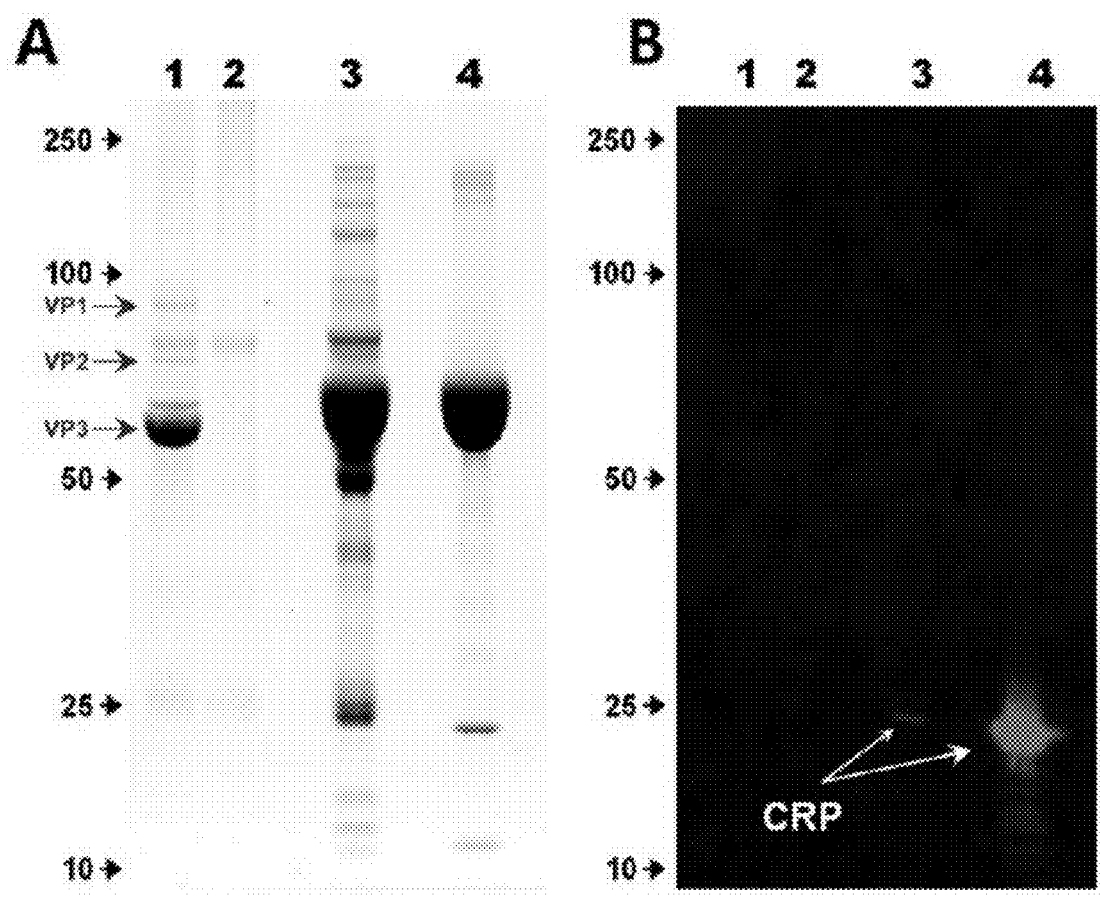
FIGS. 15A and B are images of a Coomassie stained gel of human serum proteins eluted from AVB-Sepharse beads with immobilized rAAV6 (FIG. 15A) and corresponding Western blot probed with human CRP specific antibodies (FIG. 15B). Lane 1: serum proteins recovered in the presence of rAAV-6 pre-adsorbed to AVB-Sepharose; Lane 2: serum proteins retained by AVB-Speharose beads alone.

Murine AAV6 seronegative serum was also tested for the ability to retain G3BP, as was done for human and dog serum. In contrast to the results for human and dog, G3BP in AAV6-seronegative murine serum does not interact with AAV6 (FIG. 12). It was determined, however, that in the mouse, AAV6 interacts with C-Reactive Protein (CRP). Quantitative analysis determined that 1 AAV particle interacts with about 10 CRP molecules (Quantitative estimation was done by estimation of vector quantity on the Coomassie gel using BSA as a standard and quantity of CRP was estimated by Western blot using recombinant CRP as a standard).

Example 8

Determination of Amino Acid Positions that Might be Modified for Diminishing G3BP Binding AAV1 binds substantially less G3BP compared to AAV6 (FIG. 3). Alignment of VP1 proteins of AAV1 and AAV6 shows that there are only 6 amino acids which are different between these serotypes (FIG. 13). This comparison shows one or several of these six amino acids (F129L; D418E; K531E; L584F; V598; H642N) could be modified in order to diminish G3BP binding to the resulting modified AAV6 vector to the level of AAV1 or less. In particular, the K531E substitution in the VP protein of AAV6 is of special interest since it changes charge distribution on the surface of the AAV6 vector. The production of all six single mutants of AAV6 have been previously described in Wu et al., 2006.

Example 9

Identification of Inhibitors of G3BP Binding to AAV

The ability of Galectin-3, Galectin-1, Galectin-7, or other lectins; sugars such as β-galactoside (lactose), galactose, mannose, and the like; agnostic VPs, which are recombinant viral particles from any AAV serotype (alone or in combination, in native or chimeric forms) that are capable of interacting with G3BP and acting as a decoy, murine CRP, empty AAV capsids, fragments of G3BP capable of interacting with native G3BP, or small molecules to inhibit G3BP binding to AAV is assessed.

Example 10

G3BP Limits Tissue Distribution of AAV6 In Vivo

In vivo studies in a mouse model are carried out to show that G3BP decreases tissue distribution of AAV. Alpha-sarcoglycan deficient mice or normal mice are treated with AAV6 alone, with AAV6 pre-treated with G3BP, with AAV6 treated with human serum containing G3BP, or with AAV6 treated with human serum depleted of G3BP. The α-sarcoglycan deficient mouse model is particularly useful, since, as the inventors have presently discovered, murine G3BP does not bind to AAV6 and therefore will not interfere with study of the interaction of human G3BP and AAV6 [see, Fougerousse et al. (2007), Mol Ther.; 15:53-61]. Furthermore, the vascular endothelium of α-sarcoglycan deficient mice is leakier than that in normal mice, and their muscle parenchyma is more accessible to cells and vectors.

It is determined if pretreatment of AAV6 with human G3BP, or with human serum containing G3BP, limits tissue distribution of AAV6. Tissue distribution of AAV6 is analyzed by quantifying the level of AAV6 present in target tissues by qPCR analysis of target tissues and comparing to the control group (no human G3BP treatment). Furthermore, tissue distribution will be assessed by gene transfer of a GFP reporter gene to skeletal muscle.

Example 11

Reduction of Serum Concentration of G3BP Enhances AAV Tissue Distribution In Vivo Using a canine model of muscular dystrophy (Golden Retriever Muscular Dystrophy (GRMB)), in which a splice site mutation in intron 6 accounts for the lack of functional dystrophin, tissue distribution of AAV is characterized after reducing serum concentrations of G3BP. AAV seronegative dogs are used. For reduction of serum concentration of G3BP, plasmapheresis is carried out. Effective depletion of G3BP from the serum is determined by analyzing a serum sample following G3BP depletion by ELISA. The serum concentration of G3BP is preferably reduced to a concentration of less than about 2.5 μg/ml.

Following G3BP depletion, gene therapy is carried out using an AAV6 vector expressing either a reporter gene or a therapeutic cassette made of an U7 gene designed to rescue the GRMD dystrophin. The effectiveness of the gene therapy in dogs in which G3BP has been depleted from the serum prior to administration of AAV vector is compared to the effectiveness of gene therapy in control dogs in which G3BP has not been depleted from the serum prior to AAV administration.

Example 12

CRP but not G3BP Interacts with rAAV-6 in Mouse Serum

When such experiments using immobilized rAAV-6 were carried out with mouse sera, no G3BP murine protein homolog (ie. the mouse cyclophilin C-associated protein, 68% of homology, with an apparent MW of 77 kD on SDS PAGE, and pI 5.0; (Friedman et al., 1993, Chicheportiche et al., 1994)) was found by 2D gel analysis. Instead, a protein with a MW of 24 kD was readily detected (FIG. 14 A, B) and subsequently identified by MALDI-ToF analysis as the C-reactive protein (CRP). Retention of the murine CRP by rAAV-6 was further confirmed by Western blot analysis (FIG. 14 C, D).

In contrast, the human CRP did not react with rAAV-6 (FIG. 15). Human serum proteins eluted from AVB-Sepharose beads with immobilized were fractionated by PAGE and Coomassie stained (A), transferred to PVDF membrane and analyzed by Western blot (B) with human CRP specific antibodies. Lane 1: serum proteins recovered in the presence of rAAV-6 pre-adsorbed to AVB-Sepharose; Lane 2: serum proteins retained by AVB-Speharose beads alone; Lane 3: unfractionated human serum; Lane 4: recombinant CRP (100 ng) stabilized with BSA. Human CRP did not react with rAAV-6, thus demonstrating that this peculiar serotype interacted with serum proteins in a species-specific manner.

Legend of FIG. 14: CRP, but not G3BP, Interacts with rAAV-6 in Mouse Serum.

Adsorbed mouse serum proteins eluted from AVB-Sepharose analyzed by two-dimensional gel electrophoresis (Coomassie staining) (A) Control with AVB-Sepharose alone, and (B) with 10E12 physical particles (pp) of rAAV-6 pre-adsorbed. An additional protein of about 25 kD was eluted from the AVB-Sepharose in the presence of rAAV-6 (box). MALDI-ToF analysis identified the 25 kD protein as the C-reactive protein (CRP). (C) Coomassie staining of SDS-PAGE, (D) corresponding Western blot analysis (PVDF membrane) using a goat polyclonal antibody (primary) against mouse CRP (1:1,000; R&D systems) and a species anti-goat IRDye-800CW conjugated secondary antibody (1:10,000). Lanes 1 and 2: protein extracts from mouse serum recovered via AVB-Sepharose immuno-affinity beads, loaded with rAAV-6 or buffer alone, respectively. VP1, VP2 and VP3 as well as serum CRP (around 25 kD MW) were detected in lane 1. In lane 2, beads alone did not retain CRP although some other unidentified proteins were recovered depending on washing stringency.

Legend of FIG. 15: The Human Homolog of CRP does not Interact with rAAV6.

Human serum proteins eluted from AVB-Sepharose beads with immobilized rAAV6 were fractionated by PAGE and Coomassie stained (A), transferred to PVDF membrane and analyzed by Western blot (B) with human CRP specific antibodies. Lane 1: serum proteins recovered in the presence of rAAV-6 pre-adsorbed to AVB-Sepharose; Lane 2: serum proteins retained by AVB-Sepharose beads alone; Lane 3: unfractionated human serum; Lane 4: recombinant CRP (100 ng) stabilized with BSA.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

Particular Embodiments

1. A method for increasing the efficiency of target tissue penetration of an adeno-associated virus (AAV) vector in a patient in need thereof, which method comprises abrogating or reducing the galectin 3 binding protein (G3BP)-mediated reduction of said tissue penetration.

2. The method of embodiment 1, wherein said abrogation is achieved by depletion of or by abrogation or reduction of an ability of G3BP to interact with said AAV vector.

3. The method of embodiment 2, wherein depletion is achieved ex vivo.

4. The method of embodiment 3 wherein said ex vivo depletion is achieved using at least one of chromatography, plasmapheresis, and an affinity column.

5. The method of embodiment 1, wherein said abrogation or reduction is achieved in a patient by administering a G3BP inhibitor.

6. The method of embodiment 5, wherein the inhibitor is a G3BP neutralizing antibody.

7. The method of embodiment 6, wherein the antibody is administered prior to or substantially simultaneously with exposure to said virus.

8. The method of embodiment 1, wherein said abrogation is achieved in a patient by administering a G3BP antibody.

9. The method of embodiment 8, wherein the antibody is a monoclonal antibody.

10. The method of embodiment 8, wherein the antibody is administered prior to or substantially simultaneously with exposure to said virus.

11. The method of embodiment 1, wherein said abrogation or reduction is achieved using a G3BP inhibitor selected from the group consisting of: galectins, sugars, competing isolated viral protein, murine C reactive protein, empty AAV capsids, fragments of G3BP capable of interacting with native G3BP, and small molecules.

12. The method of embodiment 5, wherein the G3BP inhibitor is provided in an amount sufficient to reduce the host's serum concentration of G3BP available to interact with the AAV vector to within the range between about 1 μg/ml and 5 μg/ml.

13. The method of embodiment 1, wherein the G3BP inhibitor is provided in an amount sufficient to reduce the host's serum concentration of G3BP available to interact with the AAV vector to within the range between about 1 μg/ml and 3 μg/ml.

14. The method of embodiment 1, wherein the G3BP inhibitor is provided in an amount effective to reduce the serum concentration of G3BP available to interact with the AAV vector to a concentration of less than about 2.5 μg/ml.

15. The method of embodiment 1, wherein said abrogation or reduction is achieved by structurally modifying AAV, wherein G3BP does not interact with said modified AAV.

16. The method of embodiment 15, wherein the structural modification involves replacing AAV capsid with an AAV9 capsid.

17. The method of embodiment 1, wherein the AAV vector is selected from the group consisting of AAV-1, AAV-2, AAV-3, AAV-4, AAV-5, AAV-6, AAV-7, AAV-8, AAV-10, and AAV-11.

18. The method of embodiment 17, wherein said AAV vector is AAV1, AAV6, or AAV8.

19. A method for reducing tissue distribution of a virus in a patient, which method comprises administering to a patient in need thereof a composition comprising galectin 3 binding protein (G3BP) in an effective amount for retaining a substantial portion of said virus in the serum.

20. The method of embodiment 19, wherein said virus is selected from the group consisting of influenza virus, HCV, HBV, adenovirus, herpes simplex virus, varicella zoster virus, cytomegalovirus, Epstein-Bar virus, measles virus, rubeola virus, respiratory syncytial virus, rotavirus, metapneumovirus, norovirus, sapovirus, mumps virus, coxsackie virus, parovirus, lyssavirus, and human immunodeficiency virus.

21. The method of embodiment 19, wherein the composition is administered intravenously.

22. The method of embodiment 21, wherein the composition is administered at a dose sufficient to achieve a serum concentration of G3BP of at least 2.5 micrograms per milliliter, in particular of at least 5 micrograms per milliliter, more particularly within the range from about 5 to about 10 micrograms per milliliter.

23. The method of embodiment 19, wherein said composition comprising G3BP is administered sequentially or simultaneously with at least one additional antiviral composition.

24. The method of embodiment 24, wherein said additional composition is one of acyclovir and interferon-ribavirin.

25. The method of embodiment 19, wherein said patient is an organ transplant patient.

26. The method of embodiment 19, wherein said virus is introduced by a transplanted organ received by said patient.

27. The method of embodiment 25, wherein said patient is administered the compositions prior to, at the time of, or after organ transplantation.

28. A method for reducing the amount of infective virus available in an organ destined for transplantation into a patient in vitro, which method comprises exposing said organ to galectin 3 binding protein (G3BP) in vitro in an effective amount for reducing the ability of said virus to achieve tissue distribution after transplantation into the patient.

29. The method of embodiment 28, wherein said G3BP is recombinant, isolated protein, or G3BP mimetic agent.

30. The method of embodiment 28, wherein said G3BP is administered to said organ by hypothermic or normothermic perfusion.

31. A method for limiting the titer of a virus that would be achieved in a patient, which method comprises administering to a patient in need thereof a composition comprising galectin 3 binding protein (G3BP) in an effective amount for limiting the titer that would be achieved of said virus in serum.

32. The method of embodiment 31, wherein said G3BP is conjugated to an anti-viral agent or anti-viral compound.

33. The method of embodiment 31, wherein said G3BP is conjugated to an antibody.

34. A method for reducing tissue distribution of a virus in a patient, which method comprises administering to a patient in need thereof a composition comprising a protein with a scavenger receptor cysteine-rich domain in an effective amount for retaining said virus in the serum.

35. A composition comprising galectin 3 binding protein (G3BP) and a pharmaceutically acceptable carrier or diluent.

36. A pharmaceutical formulation comprising a therapeutically effective amount of galectin 3 binding protein (G3BP) and a pharmaceutically acceptable carrier or diluent wherein the amount of G3BP is effective to inhibit tissue distribution of a virus in a host to whom the composition is administered.

SEQUENCE LISTING

```
SEQ ID NO: 1
galectin 3 binding protein [Homo sapiens]
GenBank Accession No. NP_005558
   1 mtpprlfwvw llvagtqgvn dgdmrladgg atnggrveif yrgqwgtvcd nlwdltdasv
  61 vcralgfena tqalgraafg qgsgpimlde vqctgteasl adckslgwlk sncrherdag
 121 vvctnetrst htldlsrels ealgqifdsq rgcdlsisvn vggedalgfc ghtviltanl
 181 eaqalwkepg snvtmsvdae cvpmvrdllr yfysrridit lssvkcfhkl asaygarqlq
 241 gycaslfail lpqdpsfqmp ldlyayavat gdalleklcl qflawnfeal tqaeawpsvp
 301 tdllqlllpr sdlavpsela llkavdtwsw gerasheeve glvekirfpm mlpeelfelq
 361 fnlslywshe alfqkktlqa lefhtvpfql larykglnit edtykpriyt sptwsafvtd
 421 sswsarksql vyqsrrgplv kyssdyfqap sdyryypyqs fqtpqhpsfl fqdkrvswsl
 481 vylptiqscw nygfscssde lpvlgltksg gsdrtiayen kalmlceglf vadvtdfegw
 541 kaaipsaldt nsskstssfp cpaghfngfr tvirpfyltn ssgvd SEQ ID NO: 2
similar to Galectin-3 binding protein precursor (Lectin galactoside-binding
soluble 3 binding protein) (Mac-2 binding protein) (Mac-2 BP)
(MAC2BP) (Tumor-associated antigen 90K) [Canis familiaris].
GenBank Accession No. XP_540405
   1 malplvlwmc llvagtqgvk dgdmrlangd tanegrveif ysgrwgtvcd nlwdlmdasv
  61 vcralgfena tealggaafg pgkgpimlde vectgtepsl anctslgwmk sncrhncidag
 121 vvcsnetrga htldlsgelp aalegifdsq rgcdlsirvk vkdgeeegph fcahrlilaa
 181 npeaqalcka pgstvtmevd aeclpvvrdf irylysrrld isltsvkcfh klasayeagq
 241 lqsfcaslfa illpedpsfq apldlyayal atqdpvleel cvqflawnfe gltqatawpr
 301 vptallqlll srselavpse lalltaldvw sgerrpshge varlvdkvrf pmmlpehlfe
 361 lqfnlslyws healfqkkil galefhtvpf rllaqhrgln ltedayqprl ytsptwsasv
 421 srsssrywny pygsfqtpqh psflfqnkyi swslvylptv qscwnygfsc ssdevpllgl
 481 sksdysdpti gyenkalmrc ggrfvadvtd fegqkalips algtnssrrp slfpclggsf
 541 ssfqvvirpf yltnssdvd SEQ ID NO: 3
RecName: Full = Galectin-3-binding protein; AltName: Full = Lectin
galactoside-binding soluble 3-binding protein; AltName:
Full = Cyp-C-associated protein; Short = CyCAP; AltName:
Full = Protein
MAMA; Flags: Precursor. [MURINE]
GenBank Accession No. Q07797
   1 mallwllsvf llvpgtqgte dgdmrlvnga sanegrveif yrgrwgtvcd nlwnlldahv
  61 vcralgyena tqalgraafg pgkgpimlde vectgtessl ascrslgwmv srcghekdag
 121 vvcsndttgl hildlsgels dalgqifdsq qgcdlfiqvt gqgyedlslc ahtlilrtnp
 181 eaqalwqvvg ssvimrvdae cmpvvrdflr yfysrrievs mssvkclhkl asaygatelq
 241 dycgrlfatl lpqdptfhtp ldlyayarat gdsmledlcv qflawnfepl tqseswsavp
 301 ttliqallpk selaysseld llkavdqwst etiashedie rlveqvrfpm mlpqelfelq
 361 fnlslyqdhq alfgrktmqa lefhtvpvev lakykglnit edtykprlyt sstwsslvma
 421 stwragryey nrynglytyg ygsvarynsy qsfqtpqhps flfkdkqisw satylptmqs
 481 cwnygfscts nelpvlgltt ssysnptigy enrvlilcgg ysvvdvtsfe gskapiptal
 541 dtnssktpsl fpcasgafss frvvirpfyl tnstdmv SEQ ID NO:4
AAV6 VP protein
MAADGYLPDW LEDNLSEGIR EWWDLKPGAP KPKANQQKQD DGRGLVLPGY KYLGPFNGLD        60
KGEPVNAADA AALEHDKAYD QQLKAGDNPY LRYNHADAEF QERLQEDTSF GGNLGRAVFQ       120
AKKRVLEPFG LVEEGAKTAP GKKRPVEQSP QEPDSSSGIG KTGQQPAKKR LNFGQTGDSE       180
SVPDPQPLGE PPATPAAVGP TTMASGGAP MADNNEGADG VGNASGNWHC DSTWLGDRVI        240
```

```
                              SEQUENCE LISTING

TTSTRTWALP  TYNNHLYKQI  SSASTGASND  NHYFGYSTPW  GYFDFNRFHC  HFSPRDWQRL      300
INNNWGFRPK  RLNFKLFNIQ  VKEVTTNDGV  TTIANNLTST  VQVFSDSEYQ  LPYVLGSAHQ      360
GCLPPFPADV  FMIPQYGYLT  LNNGSQAVGR  SSFYCLEYFP  SQMLRTGNNF  TFSYTFEDVP      420
FHSSYAHSQS  LDRLMNPLID  QYLYYLNRTQ  NQSGSAQNKD  LLFSRGSPAG  MSVQPKNWLP      480
GPCYRQQRVS  KTKTDNNNSN  FTWTGASKYN  LNGRESIINP  GTAMASHKDD  KDKFFPMSGV      540
MIFGKESAGA  SNTALDNVMI  TDEEEIKATN  PVATERFGTV  AVNLQSSSTD  PATGDVHVMG      600
ALPGMVWQDR  DVYLQGPIWA  KIPHTDGHFH  PSPLMGGFGL  KHPPPQILIK  NTPVPANPPA      660
EFSATKFASF  ITQYSTGQVS  VEIEWELQKE  NSKRWNPEVQ  YTSNYAKSAN  VDFTVDNNGL      720
YTEPRPIGTR  YLTRPL                                                         736

SEQ ID NO: 5
AAV6 VP protein with K531E substitution
MAADGYLPDW  LEDNLSEGIR  EWWDLKPGAP  KPKANQQKQD  DGRGLVLPGY  KYLGPFNGLD       60
KGEPVNAADA  AALEHDKAYD  QQLKAGDNPY  LRYNHADAEF  QERLQEDTSF  GGNLGRAVFQ      120
AKKRVLEPFG  LVEEGAKTAP  GKKRPVEQSP  QEPDSSSGIG  KTGQQPAKKR  LNFGQTGDSE      180
SVPDPQPLGE  PPATPAAVGP  TTMASGGGAP  MADNNEGADG  VGNASGNWHC  DSTWLGDRVI      240
TTSTRTWALP  TYNNHLYKQI  SSASTGASND  NHYFGYSTPW  GYFDFNRFHC  HFSPRDWQRL      300
INNNWGFRPK  RLNFKLFNIQ  VKEVTTNDGV  TTIANNLTST  VQVFSDSEYQ  LPYVLGSAHQ      360
GCLPPFPADV  FMIPQYGYLT  LNNGSQAVGR  SSFYCLEYFP  SQMLRTGNNF  TFSYTFEDVP      420
FHSSYAHSQS  LDRLMNPLID  QYLYYLNRTQ  NQSGSAQNKD  LLFSRGSPAG  MSVQPKNWLP      480
GPCYRQQRVS  KTKTDNNNSN  FTWTGASKYN  LNGRESIINP  GTAMASHKDD  EDKFFPMSGV      540
MIFGKESAGA  SNTALDNVMI  TDEEEIKATN  PVATERFGTV  AVNLQSSSTD  PATGDVHVMG      600
ALPGMVWQDR  DVYLQGPIWA  KIPHTDGHFH  PSPLMGGFGL  KHPPPQILIK  NTPVPANPPA      660
EFSATKFASF  ITQYSTGQVS  VEIEWELQKE  NSKRWNPEVQ  YTSNYAKSAN  VDFTVDNNGL      720
YTEPRPIGTR  YLTRPL                                                         736

SEQ ID NO: 6
AAV1 VP protein
MAADGYLPDW  LEDNLSEGIR  EWWDLKPGAP  KPKANQQKQD  DGRGLVLPGY  KYLGPFNGLD       60
KGEPVNAADA  AALEHDKAYD  QQLKAGDNPY  LRYNHADAEF  QERLQEDTSF  GGNLGRAVFQ      120
AKKRVLEPLG  LVEEGAKTAP  GKKRPVEQSP  QEPDSSSGIG  KTGQQPAKKR  LNFGQTGDSE      180
SVPDPQPLGE  PPATPAAVGP  TTMASGGGAP  MADNNEGADG  VGNASGNWHC  DSTWLGDRVI      240
TTSTRTWALP  TYNNHLYKQI  SSASTGASND  NHYFGYSTPW  GYFDFNRFHC  HFSPRDWQRL      300
INNNWGFRPK  RLNFKLFNIQ  VKEVTTNDGV  TTIANNLTST  VQVFSDSEYQ  LPYVLGSAHQ      360
GCLPPFPADV  FMIPQYGYLT  LNNGSQAVGR  SSFYCLEYFP  SQMLRTGNNF  TFSYTFEEVP      420
FHSSYAHSQS  LDRLMNPLID  QYLYYLNRTQ  NQSGSAQNKD  LLFSRGSPAG  MSVQPKNWLP      480
GPCYRQQRVS  KTKTDNNNSN  FTWTGASKYN  LNGRESIINP  GTAMASHKDD  EDKFFPMSGV      540
MIFGKESAGA  SNTALDNVMI  TDEEEIKATN  PVATERFGTV  AVNFQSSSTD  PATGDVHAMG      600
ALPGMVWQDR  DVYLQGPIWA  KIPHTDGHFH  PSPLMGGFGL  KNPPPQILIK  NTPVPANPPA      660
EFSATKFASF  ITQYSTGQVS  VEIEWELQKE  NSKRWNPEVQ  YTSNYAKSAN  VDFTVDNNGL      720
YTEPRPIGTR  YLTRPL                                                         736
```

REFERENCES

Barth, R. E., M. F. van der Loeff, et al. "Virological follow-up of adult patients in antiretroviral treatment programmes in sub-Saharan Africa: a systematic review." *Lancet Infect Dis* 10(3): 155-166.

Boutin, S., V. Monteilhet, et al. "Prevalence of serum IgG and neutralizing factors against adeno-associated virus types 1, 2, 5, 6, 8 and 9 in the healthy population: implications for gene therapy using AAV vectors." *Hum Gene Ther.*

Boye, S. E., Boye, S. L., Pang, J., Ryals, R., Everhart, D., Umino, Y., Neeley, A. W., Besharse, J., Barlow, R. & Hauswirth, W. W. *PLoS One* 5, e11306.

Chenail, G., Brown, N. E., Shea, A., Feire, A. L. & Deng, G. (2010) *Anal Biochem*.

Chicheportiche, Y. & Vassalli, P. (1994) *J Biol Chem* 269, 5512-7.

Denti, M. A., Rosa, A., D'Antona, G., Sthandier, O., De Angelis, F. G., Nicoletti, C., Allocca, M., Pansarasa, O., Parente, V., Musaro, A., Auricchio, A., Bottinelli, R. & Bozzoni, I. (2006) *Proc Natl Acad Sci USA* 103, 3758-63.

Denard, J., S. Rundwasser, et al. (2009). "Quantitative proteomic analysis of lentiviral vectors using 2-DE." *Proteomics* 9(14): 3666-76.

DiPrimio, N., McPhee, S. W. & Samulski, R. J. *Curr Opin Mol Ther* 12, 553-60.

Friedman, J., Trahey, M. & Weissman, I. (1993) *Proc Natl Acad Sci USA* 90, 6815-9.

Gregorevic, P., Blankinship, M. J., Allen, J. M. & Chamberlain, J. S. (2008) *Mol Ther* 16, 657-64.

Halbert C L, Madtes D K, Vaughan A E, Wang Z, Storb R, Tapscott S J, Miller A D. "Expression of human alphal-antitrypsin in mice and dogs following AAV6 vector-mediated gene transfer to the lungs." *Mol Ther.* 2010 June; 18(6):1165-72.

Hellstern, S., T. Sasaki, et al. (2002). "Functional studies on recombinant domains of Mac-2-binding protein." *J Biol Chem* 277(18): 15690-6.

Jiang X, Yang C Y, Mao M, Liu Q Q, Wang L. Sichuan Da Xue Xue Bao Yi Xue Ban. 2010 March; 41(2):203-7.

Jay, F. T., C. A. Laughlin, et al. (1981). "Eukaryotic translational control: adeno-associated virus protein synthesis is affected by a mutation in the adenovirus DNA-binding protein."*Proc Natl Acad Sci USA* 78(5): 2927-31.

Kilpatrick L A, Li Q, Yang J, Goddard J C, Fekete D M, Lang H. "Adeno-associated virus-mediated gene delivery into the scala media of the normal and deafened adult mouse ear." Gene Ther. 2011 Jan. 6. [Epub ahead of print]

Klimczak R R, Koerber J T, Dalkara D, Flannery J G, Schaffer D V. "A novel adeno-associated viral variant for efficient and selective intravitreal transduction of rat Muller cells." PLoS One. 2009 Oct. 14; 4(10):e7467.

Kornegay, J. N., Li, J., Bogan, J. R., Bogan, D. J., Chen, C., Zheng, H., Wang, B., Qiao, C., Howard, J. F., Jr. & Xiao, X. (2010) *Mol Ther* 18, 1501-8

Koths, K., Taylor, E., Halenbeck, R., Casipit, C. & Wang, A. (1993) *J Biol Chem* 268, 14245-9.

Marcelin, A. G., F. Ceccherini-Silberstein, et al. (2009). "Resistance to novel drug classes." *Curr Opin HIV AIDS* 4(6): 531-7.

Muller, S. A., T. Sasaki, et al. (1999). "Domain organization of Mac-2 binding protein and its oligomerization to linear and ring-like structures." *J Mol Biol* 291(4): 801-13.

Nogues, C., Leh, H., Langendorf, C. G., Law, R. H., Buckle, A. M. & Buckle, M. (2010) *PLoS One* 5, e12152.

Pang, J., Boye, S. E., Lei, B., Boye, S. L., Everhart, D., Ryals, R., Umino, Y., Rohrer, B., Alexander, J., Li, J., Dai, X., Li, Q., Chang, B., Barlow, R. & Hauswirth, W. W. *Gene Ther* 17, 815-26.

Penaud-Budloo, M., Le Guiner, C., Nowrouzi, A., Toromanoff, A., Cherel, Y., Chenuaud, P., Schmidt, M., von Kalle, C., Rolling, F., Moullier, P. & Snyder, R. O. (2008) *J Virol* 82, 7875-85.

Polyak, S., Mah, C., Porvasnik, S., Herlihy, J. D., Campbell-Thompson, M., Byrne, B. J. & Valentine, J. F. (2008) *Dig Dis Sci* 53, 1261-70.

Rolling, F. and R. J. Samulski (1995). "AAV as a viral vector for human gene therapy. Generation of recombinant virus." *Mol Biotechnol* 3(1): 9-15.

Ruffing, M., H. Zentgraf, et al. (1992). "Assembly of virus-like particles by recombinant structural proteins of adeno-associated virus type 2 in insect cells." *J Virol* 66(12): 6922-30.

Sasaki, T., Brakebusch, C., Engel, J. & Timpl, R. (1998) *Embo J* 17, 1606-13.

Smith, R. H., J. R. Levy, et al. (2009). "A simplified baculovirus-AAV expression vector system coupled with one-step affinity purification yields high-titer rAAV stocks from insect cells." *Mol Ther* 17(11): 1888-96.

Ussher J E, Taylor J A. "Optimized transduction of human monocyte-derived dendritic cells by recombinant adeno-associated virus serotype 6." *Hum Gene Ther.* 2010 December; 21(12): 1675-86.

Virag, T., S. Cecchini, et al. (2009). "Producing recombinant adeno-associated virus in foster cells: overcoming production limitations using a baculovirus-insect cell expression strategy." *Hum Gene Ther* 20(8): 807-17.

Wu Z, Asokan A, Grieger J C, Govindasamy L, Agbandje-McKenna M, Samulski R J. "Single amino acid changes can influence titer, heparin binding, and tissue tropism in different adeno-associated virus serotypes." J. Virol. 2006 November; 80(22):11393-7. Epub 2006 Aug. 30.

The invention claimed is:

1. A method for increasing the efficiency of target tissue penetration of an adeno-associated virus (AAV) vector upon administration of said vector to a patient in need thereof, which method comprises abrogating the galectin 3 binding protein (G3BP)-mediated reduction of said tissue penetration by depleting said G3BP.

2. The method of claim 1, wherein said depletion is achieved using at least one of chromatography, pl